(12) United States Patent
Vo-Dinh

(10) Patent No.: US 6,174,677 B1
(45) Date of Patent: *Jan. 16, 2001

(54) ADVANCED SURFACE-ENHANCED RAMAN GENE PROBE SYSTEMS AND METHODS THEREOF

(75) Inventor: Tuan Vo-Dinh, Knoxville, TN (US)

(73) Assignee: UT-Battelle, LLC, Oak Ridge, TN (US)

( * ) Notice: Under 35 U.S.C. 154(b), the term of this patent shall be extended for 0 days.

This patent is subject to a terminal disclaimer.

(21) Appl. No.: 09/161,897

(22) Filed: Sep. 28, 1998

Related U.S. Application Data

(63) Continuation-in-part of application No. 08/543,212, filed on Oct. 13, 1995, now Pat. No. 5,814,516.

(51) Int. Cl.[7] .............................. C12Q 1/68; C12M 1/34; G01J 3/44
(52) U.S. Cl. .................. 435/6; 435/287.2; 435/287.9; 435/288.7; 356/301
(58) Field of Search .................. 435/6, 287.2, 287.9, 435/288.7; 935/77, 78; 356/301

(56) References Cited

U.S. PATENT DOCUMENTS

| | | | |
|---|---|---|---|
| 4,674,878 | 6/1987 | Vo-dinh | 356/301 |
| 5,266,498 | 11/1993 | Tarcha et al. | 436/525 |
| 5,306,403 | 4/1994 | Vo-Dinh | 204/182.8 |
| 5,325,342 | 6/1994 | Vo-Dinh | 369/13 |
| 5,341,215 | 8/1994 | Seher | 356/445 |
| 5,376,556 | 12/1994 | Tarcha et al. | 436/525 |
| 5,400,136 | 3/1995 | Vo-Dinh | 356/301 |
| 5,445,972 | 8/1995 | Tarcha et al. | 436/544 |

FOREIGN PATENT DOCUMENTS 0 667 398 A2   8/1998   (EP) .

OTHER PUBLICATIONS

Graham et al., "Selective detection of deoxyribonucleic acid at ultralow concentrations by SERRS", Analytical Chemistry, vol. 69, pp. 4703–4707, Nov. 1997.*

Matthews et al., "Analytical strategies for the use of DNA probes", Analytical Biochemistry, vol. 169, pp. 1–25, 1988.*

Jeanmaire, D. L. et al, "Surface Raman Spectroelectrochemistry. Part I. Heterocyclic, Aromatic, & Aliphatic Amines Adsorbed on the Anodized Silver Electrode," *J. Electroanal. Chem.*, 84 (1977) 1–20.

Sambrook, J. et al, *Molecular Cloning*, a Laboratory Manual, $2^{nd}$ ed., Cold Spring Harbon Laboratory Press, 1989.

(List continued on next page.)

Primary Examiner—Jeffrey Fredman
Assistant Examiner—Arun Chakrabarti
(74) Attorney, Agent, or Firm—Shelley L. Stafford

(57) ABSTRACT

The subject invention is a series of methods and systems for using the Surface-Enhanced Raman (SER)-labeled Gene Probe for hybridization, detection and identification of SER-labeled hybridized target oligonucleotide material comprising the steps of immobilizing SER-labeled hybridized target oligonucleotide material on a support means, wherein the SER-labeled hybridized target oligonucleotide material comprise a SER label attached either to a target oligonucleotide of unknown sequence or to a gene probe of known sequence complementary to the target oligonucleotide sequence, the SER label is unique for the target oligonucleotide strands of a particular sequence wherein the SER-labeled oligonucleotide is hybridized to its complementary oligonucleotide strand, then the support means having the SER-labeled hybridized target oligonucleotide material adsorbed thereon is SERS activated with a SERS activating means, then the support means is analyzed.

107 Claims, 17 Drawing Sheets

OTHER PUBLICATIONS

Whitesides, G. M. et al, "Wet Chemical Approaches to the Characterization of Organic Surfaces: Self–Assembled Monolayers, Wetting, and the Physical–Organic Chemistry of the Solid–Liquid Interface," *Langmuir*, 1990, 6, 87–96.

Cheng, YF et al, "Charge–Coupled Device Fluorescence Detection for Capillary–Zone Electrophoresis (CCD–CZE)," *Applied Spectroscopy*, vol. 44, No. 5, 1990, 755–765.

Piccard, RD et al, "A Multi–Optical–Fiber Array with Charge–Coupled Device Image Detection for Parallel Processing of Light Signals and Spectra," *Rev. Sci. Instrum.* 63 (3), Mar. 1991, 584–594.

Chartier–Harlin, MC et al, "Early–Onset Alzheimer's Disease Caused by Mutations at Codon 717 of the β–Amyloid Precursor Protein Gene," *Nature*, vol. 353, 1991, 744–846.

Li, Y. S. et al, "Surface–Enhanced Raman Analysis of p–Nitroaniline on Vacuum Evaporation and Chemically Deposited Silver–Coated Alumina Substrates," *Applied Spectroscopy*, vol. 46, No. 9, 1992, 1354–1357.

Miki, Y. et al, "A Strong Candidate for the Breast and Ovarian Cancer Susceptibility Gene BRCA1," *Science*, vol. 266, 1994, 66–71.

Vo–Dinh, T. et al, "Surface–Enhanced Raman Gene Probes," *Anal. Chem.*, vol. 66, No. 20, 1994, 3379–3383.

Pal, A. et al, "Selective Surface–Enhanced Raman Spectroscopy Using a Polymer–Coated Substrate," Anal. Chem. (1995) 67 (18) 3154–9.

Vo–Dinh, T., "Surface–Enhanced Raman Scattering," *Photonic Probes of Surfaces*, edited by P. Halevi, 1995.

Vo–Dinh, T., "Surface–Enhanced Raman Spectroscopy Using Metallic Nanostructures, "*Anal. Chem.*, vol. 17, No. 8+9, 1998, 557–582.

B. C. F. Chu et al, "Derivatization of Unprotected Polynucleotides," *Nucleic Acids Research*, vol. 11, #18, 1983.

M. Stoffel et al, "Human Glucokinase Gene: Isolation, Characterization, and Identification of Two Missense Mutations Linked to Early–Onset Non–Insulin–Dependent (Type 2) Diabetes Mellitus," *Proc. Natl. Acad. Sci. USA*, vol. 89, pp. 7698–7702, Aug. 1992.

M. Eriksson, "Structure of PNA–Nucleic Acid Complexes," *Nucleosides & Nucleotides*, 16(5&6), 617–621, 1997.

* cited by examiner

ADVANCED SURFACE-ENHANCED RAMAN GENE PROBE SYSTEMS AND METHODS THEREOF

CROSS-REFERENCED APPLICATIONS AND PATENTS

The present application is a Continuation-In-Part Application of co-pending U.S. patent application Ser. No. 08/543,212 filed Oct. 13, 1995, to issue as U.S. Pat. No. 5,814,516, incorporated herein by reference.

This invention was made with Government support under contract DE-AC05-84OR21400 awarded by the Office of Health and Environmental Research, Department of Energy to Lockheed Martin Energy Systems, Inc., and the Government has certain rights in this invention.

FIELD OF THE INVENTION

The present invention relates to non-radioactive DNA gene probe systems, biosensors and methods for gene identification, particularly to non-radioactive gene probes, biosensors and methods for hybridization, detection and identification of hybridized oligonucleotides based on surface-enhanced Raman scattering (SERS) label detection, and more particularly to advanced SER gene probe systems, biosensors, detection systems and methods for detecting hybridized SER gene probes utilizing substrates and membranes suitable for hybridization or blotting materials.

BACKGROUND OF THE INVENTION

There is currently strong interest in the development of nonradioactive deoxyribonucleic acid (DNA) probes for use in a wide variety of applications, such as gene identification, gene mapping, DNA sequencing, medical diagnostics, and biotechnology. Among the various methods for gene identification, technologies using radioactive labels are currently the most widely used. Radioactive label techniques suffer from several disadvantages however. The principal isotope used, Phosphorus-32, has a limited shelflife because it has a 14-day half-life. Secondly, because there is one principal label for gene probes, DNA can only be probed for one sequence at a time. Due to material limitations, probing immobilized DNA with different $^3$P-labeled sequences can only be performed a few (3–4) times. Therefore, the researcher must have idea about the sequence prior to probing. In addition to these inconveniences, the potential safety hazard associated with use of radioactive materials makes the technology undesirable. Shipping, handling and waste disposal of radioactive materials are strictly regulated by federal and state guidelines.

Recently, luminescence labels such as fluorescent or chemiluminescent labels have been developed for gene detection. Although sensitivities achieved by luminescence techniques are adequate, alternative techniques with improved spectral selectivities must be developed to overcome the need for radioactive labels and the poor spectral specificity of luminescent labels.

Spectroscopy is an analytical technique concerned with the measurement of the interaction of radiant energy with matter and with the interpretation of the interaction both at the fundamental level and for practical analysis. Interpretation of the spectra produced by various spectroscopic instrumentation has been used to provide fundamental information on atomic and molecular energy levels, the distribution of species within those levels, the nature of processes involving change from one level to another, molecular geometries, chemical bonding, and interaction of molecules in solution. Comparisons of spectra have provided a basis for the determination of qualitative chemical composition and chemical structure, and for quantitative chemical analysis.

Vibrational spectroscopy is a useful technique for characterizing molecules and for determining their chemical structure. The vibrational spectrum of a molecule, based on the molecular structure of that molecule, is a series of sharp lines which constitutes a unique fingerprint of that specific molecular structure.

One particular spectroscopic technique, known as Raman spectroscopy, utilizes the Raman effect, which is a phenomenon observed in the scattering of light as it passes through a material medium, whereby the light suffers a change in frequency and a random alteration in phase. When exciting optical energy of a single wavelength interacts with a molecule, the optical energy scattered by the molecule contains small amounts of optical energy having wavelengths different from that of the incident exciting optical energy. The wavelengths present in the scattered optical energy are characteristic of the structure of the molecule, and the intensity of this optical energy is dependent on the concentration of these molecules.

Raman spectroscopy is a spectrochemical technique that is complementary to infrared spectroscopy, and has been an important analytical tool due to its excellent specificity for chemical group identification. Raman spectroscopy provides a means for obtaining similar molecular vibrational spectra over optical fibers using visible or near infrared light that is transmitted by the optical fibers without significant absorption losses. In Raman spectroscopy, monochromatic light is directed to a sample and the spectrum of the light scattered from the sample is determined.

Raman spectroscopy is a useful tool for chemical analysis due to its excellent capability of chemical group identification. One limitation of conventional Raman spectroscopy is its low sensitivity, often requiring the use of powerful and costly laser sources for excitation. However, a renewed interest has recently developed among Raman spectroscopists as a result of observation that Raman scattering efficiency can be enhanced by factors of up to 108 or more when a compound is adsorbed on or near special metal surfaces. Spectacular enhancement factors due to the microstructured metal surface scattering process is responsible for increasing the intrinsically weak normal Raman scattering (NRS). The technique associated with this phenomenon is known as surface-enhanced Raman scattering (SERS) effect which can increase the Raman signal as well as the resonance Raman signal significantly. When the laser excitation wavelength occurs in the ultraviolet absorption band, the Raman signal of the analyte is enhanced and often called resonance Raman scattering (RRS) signal. The Raman enhancement process is believed to result from a combination of several electromagnetic and chemical effects between the molecule and the metal surface.

Deoxyribonucleic acid is the main carrier of genetic information in most living organisms. DNA is essentially a complex molecule built up of deoxyribonucleotide repeating units. Each unit comprises a sugar, phosphate, and a purine or pyrimidine base. The deoxyribonucleotide units are linked together by the phosphate groups, joining the 3' position of one sugar to the 5' position of the next. The alternate sugar and phosphate residues form the backbone of the molecule, and the purine and pyrimidine bases are attached to the backbone via the 1' position of the deoxyribose. This sugar-phosphate backbone is the same in all DNA molecules. What gives each DNA its individuality is the sequence of the purine and pyrimidine bases. Peptide nucleic acid (PNA) is a DNA analog that combines sequence specific binding to genetic targets with biostability and synthetic versatility (M. Ericson, *Nucleosides and Nucleotides*, 16 (1997), p. 617). Molecular probes (DNA, RNA and PNA) having a SERS label provide an excellent combination of detection sensitivity and spectral selectivity, important for many bioassays.

OBJECTS OF THE INVENTION

It is an object of the subject invention to provide a SER gene probe detection system for the detection and identification of biotargets such as Deoxyribonucleic acid (DNA), Ribonucleic acid (RNA) and Peptide nucleic acid (PNA) for the detection of bacteria and viruses and for medical diagnostics.

It is another object of the invention to provide methods for using a SER gene probe for hybridization, detection and identification of hybridized target oligonucleotides such as DNA, RNA and PNA related to bacteria, viruses and genetic material in a variety of samples such as environmental, biological samples or clinical samples.

It is still yet another object of the invention to provide methods for using a SER gene probe for hybridization, detection and identification of hybridized target oligonucleotides such as DNA, RNA and PNA related to bacteria, viruses and genetic material in a variety of samples using substrates suitable for hybridization, membranes and blotting materials.

It is a further object of the invention to provide methods for using a SER gene probe for use in diagnostics of genetic disease, DNA polymorphism, drug screening and drug discovery.

It is still a further object of the invention to provide methods for using a SER gene probe for DNA mapping and sequencing using yeast artificial chromosome (YAC), bacterial artificial chromosome (BAC) and P1 artificial chromosome (PAC) methods.

It is another object of the invention to provide a method for SER activating a support means such as a substrate or a membrane suitable for hybridization or a blotting material after hybridization has occurred.

It is yet another object of the invention to provide a method for SER activating a support means such as a substrate or a membrane suitable for hybridization or a blotting material simultaneously with the hybridization step.

Further and other objects of the present invention will become apparent from the description contained herein.

SUMMARY

The subject invention is a series of methods and systems using a SER gene probe for hybridization, detection and identification of SER-labeled hybridized target oligonucleotide material. The SER-labeled gene probe is used for the detection and identification of biotargets, oligonucleotide material, such as DNA, RNA and PNA related to bacteria, viruses and genetic material in a variety of samples such as environmental, biological samples or clinical samples.

In acccordance with one object of the invention, a method for using a SER-labeled gene probe for hybridization, detection and identification of SER-labeled hybridized target oligonucleotide material comprising the steps of disposing a gene probe oligonucleotide strand, being complementary to a target oligonucleotide strand, onto a support means and incubating for a period of time sufficient enough to immobilize the gene probe on the support means; then incubating the support means in an amount of solution comprising at least one SER-labeled oligonucleotide strand of unknown sequence taken from a target sample being suspect of containing target oligonucleotide strands, with the SER-labeled oligonucleotide strand having at least one SER label, incubated for a time sufficient as for the SER-labeled target oligonucleotide strands to hybridize with the immobilized gene probe oligonucleotide strands to produce SER-labeled hybridized target oligonucleotide material; then removing the SER-labeled oligonucleotide strands that did not hybridize to the immobilized gene probes; activating the support means with a SER activating means and then analyzing the SER-activated support means having SER-labeled hybridized target oligonucleotide material.

In accordance with another object of the invention, a method for using a SER-labeled gene probe for hybridization, detection and identification of SER-labeled hybridized target oligonucleotide material comprising exposing a support means to a target sample suspected of containing target oligonucleotide strands of unknown sequence and then incubating for a period of time sufficient enough to immobilize the oligonucleotide strands on the support means; synthesizing SER-labeled gene probes wherein a SER-labeled gene probe comprises at least one oligonucleotide strand of known sequence labeled with at least one SER label unique for the target oligonucleotide strands of a particular sequence; then incubating the support means having immobilized oligonucleotide strands thereon in an amount of the SER-labeled gene probe solution sufficient enough to provide an amount of SER-labeled gene probes to contact the immobilized oligonucleotide strands and sufficient enough as for hybridization to occur between the SER-labeled gene probes and the immobilized target oligonucleotide strands, thereby producing SER-labeled hybridized target oligonucleotide material; then removing excess oligonucleotide strands that did not hybridize; activating the support means with a SERS activating means and then analyzing the SER-activated support means having SER-labeled hybridized target oligonucleotide material.

In accordance with yet another aspect of the present invention, a method for using SER-labeled gene probe for hybridization, detection and identification of SER-labeled hybridized target oligonucleotide material comprising exposing a support means to a target sample suspected of containing target oligonucleotide strands of unknown sequence; then incubating to immobilize the oligonucleotide strands on the support means; then incubating the support means in an amount of solution comprising at least one gene probe of known sequence being complementary to the target oligonucleotide strand and the solution further comprising a SER label in a free state in the solution, incubating for a period of time sufficient enough as for the gene probes to contact the immobilized oligonucleotide strands and sufficient enough as for hybridization to occur between the gene probe oligonucleotide strands and the complementary immobilized target oligonucleotide strands, and sufficient enough as during hybridization, the SER label is intercalated between the hybridized oligonucleotide strands to produce SER-labeled hybridized oligonucleotide material; then removing excess oligonucleotide strands that did not hybridize; activating the support means with a SERS activating means and analyzing the SER-activated support means having SER-labeled hybridized target oligonucleotide material.

BRIEF DESCRIPTION OF THE DRAWINGS

For a better understanding of the present invention, together with other and further objects, advantages and capabilities thereof, reference is made to the following disclosure and appended claims when read in connection with the appended drawings, wherein:

DETAILED DESCRIPTION OF THE INVENTION

Figure 1:
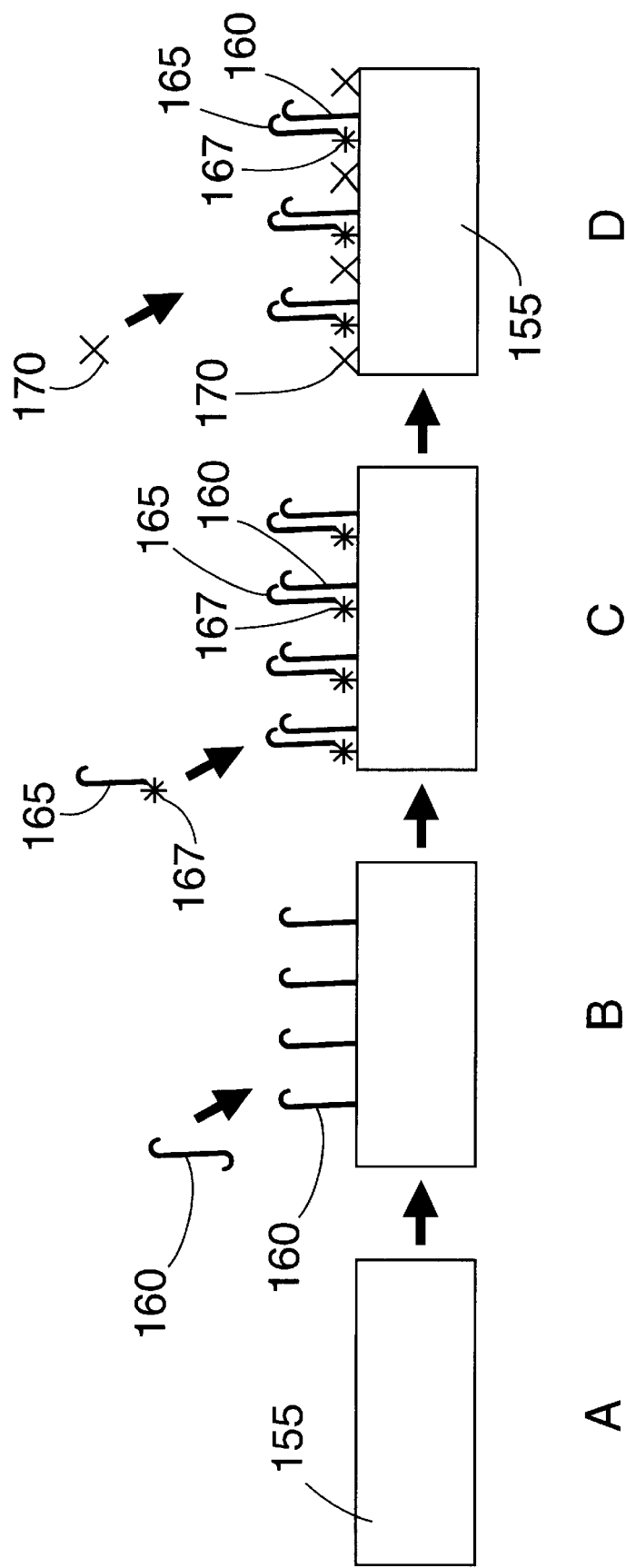
FIG. 1 shows one embodiment of the post hybridization activation method.

The possibility of using Raman and/or SERS for in situ monitoring has been reported in the past few years as well as development of efficient SER-active substrates for trace organic analysis in environmental and biological applications. The SERS technique has also been applied to trace detection of pesticides, dyes, food products, and metabolites of chemical exposure (see, Vo-Dinh, *Trends in Analytical Chemistry*, 1998, in press, incorporated herein by reference). The main advantage of Applicant's SER gene probe technique is the extremely narrow spectral bandwidth of the Raman signal from the SER label.

A modern field of research involve the discovery of new drugs using high-throughput multiplex systems. The potential of automated and combinatorial chemistry produces millions of new structures. The analysis of these drugs requires high-throughput and highly multiplex sensing. The use of SER gene probe technology provides this highly multiplex approach. Raman spectroscopy is ideal for providing the label-multiplex capability due to the sharpness of Raman peaks. Potentially, SERS offers many more unique labeling opportunities. Because the Raman spectra is based upon vibration modes, small changes in chemical structure may provide unique Raman bands. Therefore, it may be possible to modify a single SERS-active structure (with appropriate reactive groups for attachment to DNA) and thereby produce a series of SER probes with unique SERS spectra, but similar chemical reactivity.

An integral part of the human genome project is the ability to obtain large insert clones of DNA that correspond to specific regions of the human genome, thus providing a high-resolution physical map of each of the human chromosomes. Eventually, these maps will be composed of overlapping fragments of human DNA and will allow the direct acquisition of DNA fragments that correspond to specific genes The use of stable clone resources containing large human DNA inserts has opened new possibilities to contig building. Human chromosomes have been mapped on the basis of a variety of markers and resources including sequence-tagged sites (ST's) and yeast artificial chromosomes (YACs). Currently, large numbers of STSs and expressed sequence tags (ESTs) are being generated and localized on human chromosomes, and it is expected that a human chromosome with markers spaced at 100-kb intervals will soon be available. A unique approach that facilitates large-scale genomic sequencing involves transforming YAC-based maps of human chromosomes into maps based on large insert bacterial clones, such as bacterial artificial chromosomes (BACs). BACs are stable, represent the largest human inserts obtainable amongst bacterial clones, and can be readily manipulated and directly used as sequencing substrates. In order to establish the BAC approach, it is desirable to develop techniques and formats that can detect multiple BAC clone probes simultaneously.

Multiplexing is the key to technological breakthroughs in modern biological experiments including genome characterization that requires large number of samples and highly repetitive operations. The goal of the human genome project is to complete the physical mapping and sequencing of the genomes of human and several model organisms. The large genome sizes of these organisms have imposed an unprecedented amount of work that will require improved technology and streamlined strategy to achieve within a reasonable budget and time. Mapping the entire human genome using BAC librarie is a typical large-scale genomic project. The most important factor in determining the efficiency of multiplexing approaches is how many distinct labels are available, that can be used simultaneously in single experiments. Currently available fluorescence-based multiplexing allows for a limited number (four) different color dyes that can be resolved in single-pass scanning. The advantage of SERS is the potentially large number of distinct labeling molecules that generate very sharp peaks. Theoretically, up to hundreds of different types of SERS molecules can be made available. The emphasis of Applicant's SER gene technology is on the SERS detection technique which offers multiplex capability and minimizes the time and expense of gene mapping/sequencing efforts by combining the BAC mapping approach with SERS "label multiplex" detection.

Applicant's subject invention herein discloses the use of the SERS technique wherein the SER gene probe technology is used directly on nonSER-active support means such as standard hybridization substrates or any other substrates or membranes that are suitable for hybridization or blotting materials rather than SER active substrates. The support means are then subsequently made SER-active either after hybridization or simultaneously with hybridization. Polymerase Chain Reaction (PCR) or some other means for amplifying oligonucleotide material can also be used in conjunction with the hybridization steps. The present invention allows for the performance of all hybridization and PCR (optional) using substrates, membranes or blotting materials to be either followed by SER "activation" of the support means or simultaneous SER activation using the appropriate procedure as described by Applicant's subject invention.

The present invention introduces multiple methods and systems of SER activation of nonSER-active support means. One method comprises "post-hybridization activation" (PHA) and the other method comprises "simultaneous hybridization activation" (SHA). The present invention opens the possibility for extending the SER gene probe technology to many existing DNA assays that use standard hybridization substrates, membranes or blotting materials. Hybridization of a nucleic acid probe to DNA biotargets such as gene sequences, bacteria and viral DNA permits a very high degree of accuracy for identifying DNA sequences complementary to that probe.

Applicant's SER gene probe technology can rapidly detect microorganisms from multiple environmental samples. Examples include detection of Salmonella bacteria, the causative agent for food poisoning, during food processing; detection of Legionaella bacteria, the causative agent for pneumonia, from water samples; detection of Giardlia lamblia, causative agent for diarrhea, from water samples; and detection of Hepatitis virus from shellfish. Applicant's SERS gene probe biosensor can also have a global impact on biosensor technology in cancer detection. Applicant's biosensor is able to detect both DNA and RNA viruses and retroviruses in particular which can play a part in transforming healthy cells into cancer cells. Examples of this global impact include the detection of DNA viruses such as Papovavirus and its many strains which play a part in causing benign warts and carcinoma of uterine cervix worldwide. The detection of Hepadnavirus (Hepatitis B), which plays a part in causing liver cancer mainly in southeast Asia and tropical Africa, is now possible. Also, the detection of Herpesvirus, which plays a role in causing lymphocyte cancer and nasopharyngeal carcinoma mainly in west Africa, southern China and Greenland. Applicant's probe can also make a global impact on the detection of the HIV-1 virus, the causative agent for Kaposi's carcinoma and AIDS, worldwide. Another example is the detection of human T-cells and HTLV-1 virus which play a part in adult T-cell mainly in Japan (Kyushu) and detection of leukemia/lymphoma, mainly in the West Indes. Applicant's probe is a sensitive DNA biosensor that can detect viral diseases at the early stage of the infection. Yet other viruses and bacteria that can be detected are included in the causative agents that play a role in AIDS, Lyme Disease, Rocky Mountain Spotted Fever, Tuberculosis, Toxoplasmosis and Cancer. These bacteria and viruses can dwell in numerous different mediums which can be analyzed by Applicant's SER gene probe biosensor. These different mediums include bodily fluids, blood, sputum, cat feces, raw meat and other tissues. Applicant's SER gene technology using nonSER-active support means can also be used to detect genetic diseases, as well as DNA polymorphism and genetic susceptibility to disease (e.g. cancer, heart disease, diabetes, etc.).

Another application of the present SER gene technology is in DNA sequencing and mapping using SER gene probes. Yet another application of the SER gene technology involves drug discovery using high throughput screening methods which require label multiplexing.

Figure 2:
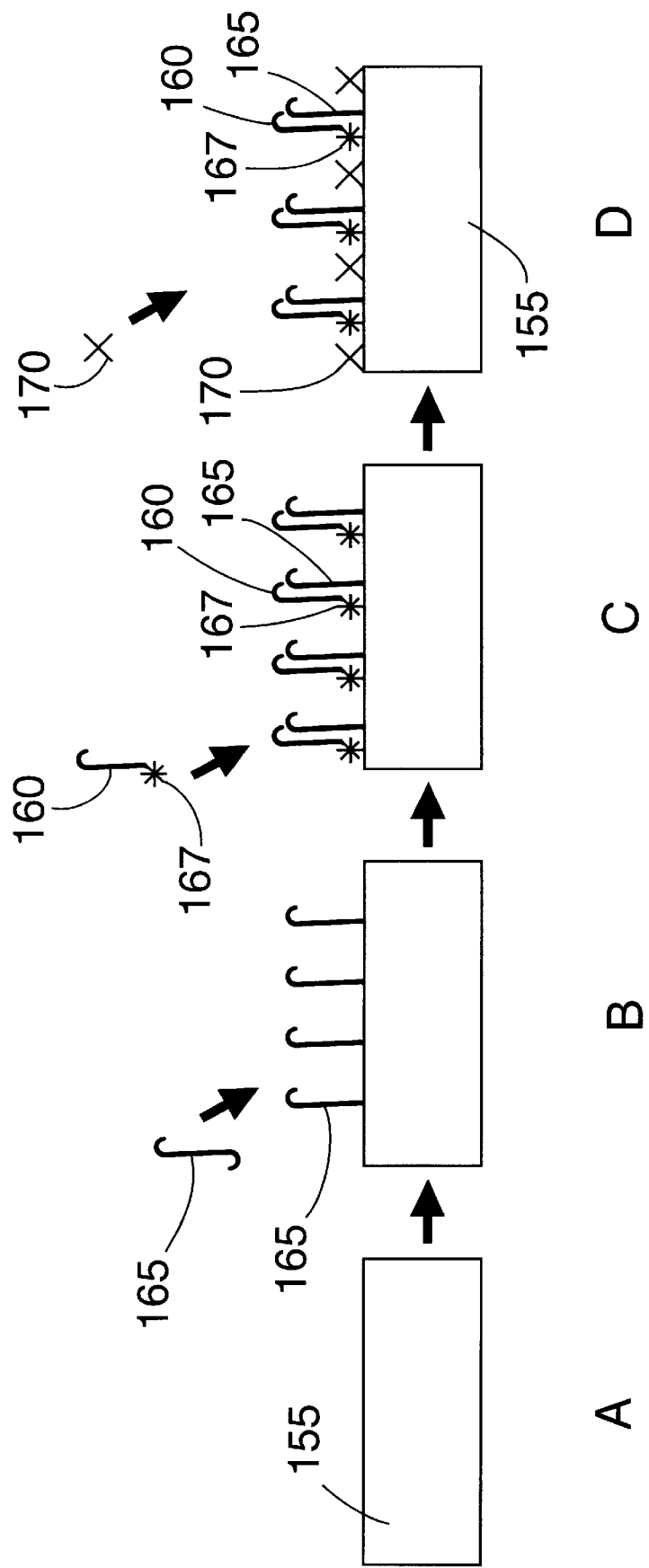
FIG. 2 shows another embodiment of the post hybridization activation method.

Applicant's previous method described in Applicant's parent application used a SER active substrate before hybridization occurred wherein the oligonucleotide strand that was to be hybridized was immobilized on the SER active substrate prior to hybridization. Applicant's present invention is a method for using a SER gene probe for the detection and identification of hybridized oligonucleotide strands labeled with a SER label wherein identification of a target oligonucleotide is based on the detection of the SER label. The SER gene probe biosensor comprises a support means and a SER gene probe hybridized with a target oligonucleotide strand adsorbed onto the support means. The support means can be any substrate suitable for hybridization or membrane suitable for hybridization or blotting material. The support means is initially not SER active. Therefore, any standard substrate can be used, such as nylon, cellulose, glass, plastic or other surface suitable for hybridization. Then, the support means is SER activated either by the PHA method as shown in FIG. 1 through FIG. 6 or the SHA method as illustrated in FIG. 8 through FIG. 13. In FIG. 1, the support means 155 has at least one oligonucleotide strand of unknown sequence 160, taken from a target sample suspected of containing target oligonucleotides, immobilized thereon when the support means 155 is incubated with a sufficient amount of target sample. In applicant's method, the immobilized oligonucleotide strand can either be of a known sequence 165 (probe) complementary to a target oligonucleotide (as in FIG. 2) or the immobilized oligonucleotide is an oligonucleotide of unknown sequence 160 (as shown in FIG. 1). The SER label 167 can be applied to either the known oligonucleotide probe 165 or the unknown oligonucleotide strand 160. In FIG. 1, the support means 155 having immobilized oligonucleotide strands of unknown sequence 160 adsorbed thereon is then incubated with a solution of oligonucleotide probes of known sequence 165 having a SER label 167, wherein the immobilized target oligonucleotide strands 160 hybridize with the SER gene probes 165,167. Then, the support means 155 is SER activated by using a SER activating means 170. FIG. 2 illustrates an alternate method whereby the probe oligonucleotides of known sequence 165, which is complementary to the sequence of the target oligonucleotide 160, is first immobilized on the support means 155 prior to hybridization. Then the support means having the probe 165 immobilized thereon is incubated with a solution of SER-labeled 167 oligonucleotides of unknown sequence 160 for a time sufficient for hybridization to occur between the immobilized probe oligonucleotides 165 and the SER-labeled 167 target oligonucleotides 160 to produce hybridized target oligonucleotide material. Then the support means 155 is SER activated by a SER activating means 170.

One example of a SER activating means is coating the support means with a solution of silver sol or silver nanoparticles (or some other metal, such as gold) 170 using thermal evaporation directly on the samples and the SERS signals from the SER label such as cresyl fast violet, is detected. Another SER activating means includes coating the surface of the support means with metal-coated magnetic nanobeads that allow the use of magnetic fields for manipulation of the hybridized oligonucleotide material. Other means by which to SER activate the support means includes spraying reagent to form silver sols (or other metal sols such as gold) onto the support means, chemical deposition, dipping the support means into a solution of silver sol (or other metal such as gold) or by any other delivery means that may be utilized to SER activate the support means. One method comprises delivering onto the substrate a solution of metal nanoparticles of metal sol, such as silver or gold. In this method, a solution of silver sol, previously prepared (preparation details given by Vo-Dinh, Surface-Enhanced Raman Spectroscopy, in *Photonic Probes of Surfaces*, P. Halevi, Ed., Elsevier, New York, 1995, incorporated herein by reference), is delivered on to the support means having hybridized products with SER-active labels. A dipping procedure may also be used wherein the support means having hybridized products with SER-active labels is dipped into the solution of particulate silver sol. Another alternative includes producing the formation of silver sol directly onto the support means having the hybridized products with SER-active labels thereon. In one embodiment, a solution of hybridized product with SER-active labels is prepared in which nanoparticles of silver sol is added into the solution or alternatively, the silver sol nanoparticles are formed in the solution of the hybridized oligonucleotides having SER-active labels.

A second embodiment of PHA is to immobilize at least one already hybridized oligonucleotide strand, wherein the SER-labeled or unlabeled known oligonucleotide strand (probe) is hybridized with the unlabeled or SER-labeled target oligonucleotide strand prior to immobilization, onto the support means, then SER activate the support means. Both of these embodiments can be performed in conjunction with PCR steps for amplification of the target oligonucleotide strands or without PCR steps if the detection sensitivity is sufficient.

Different SER labels can be used for different target oligonucleotide strands of different sequences and different bacterial and viral types. Examples of SER labels that can be used include cresyl fast violet (CFV), cresyl blue violet, brilliant cresyl blue (BCB), para-aminobenzoic acid, erythrosin, as well as aminoacridine. Other SER labels that can be used that are inert to hybridization are chemical elements or structures that exhibit a characteristic Raman or SERS emission, as long as the label doesn't interfere with hybridization. The chemical structure or substituent to be used as a SER label is not present in the original native DNA. Some chemical structures that can be used as a SER label and are inert to hybridization include cyanide (CN), thiol group (SH), chlorine (Cl), bromine (Br), a methyl group and phosphorus (P) and sulfur. The SER label can be attached at the end of the oligonucleotide strand or it can be disposed with the oligonucleotide strand. More than one SER label can be used on a given oligonucleotide strand. The SER label can be attached or disposed with either the probe oligonucleotide strand or the target oligonucleotide strand. Another embodiment is one in which two oligonucleotide strands are used for the SER gene probe and the SER label is disposed intercalated between the probe oligonucleotide strand and the target oligonucleotide strand. This particular embodiment provides the label to be held in place by the two strands. There is no attachment of the label on the oligonucleotide strands. More than one SER label may be used for this embodiment as well.

Figure 3:
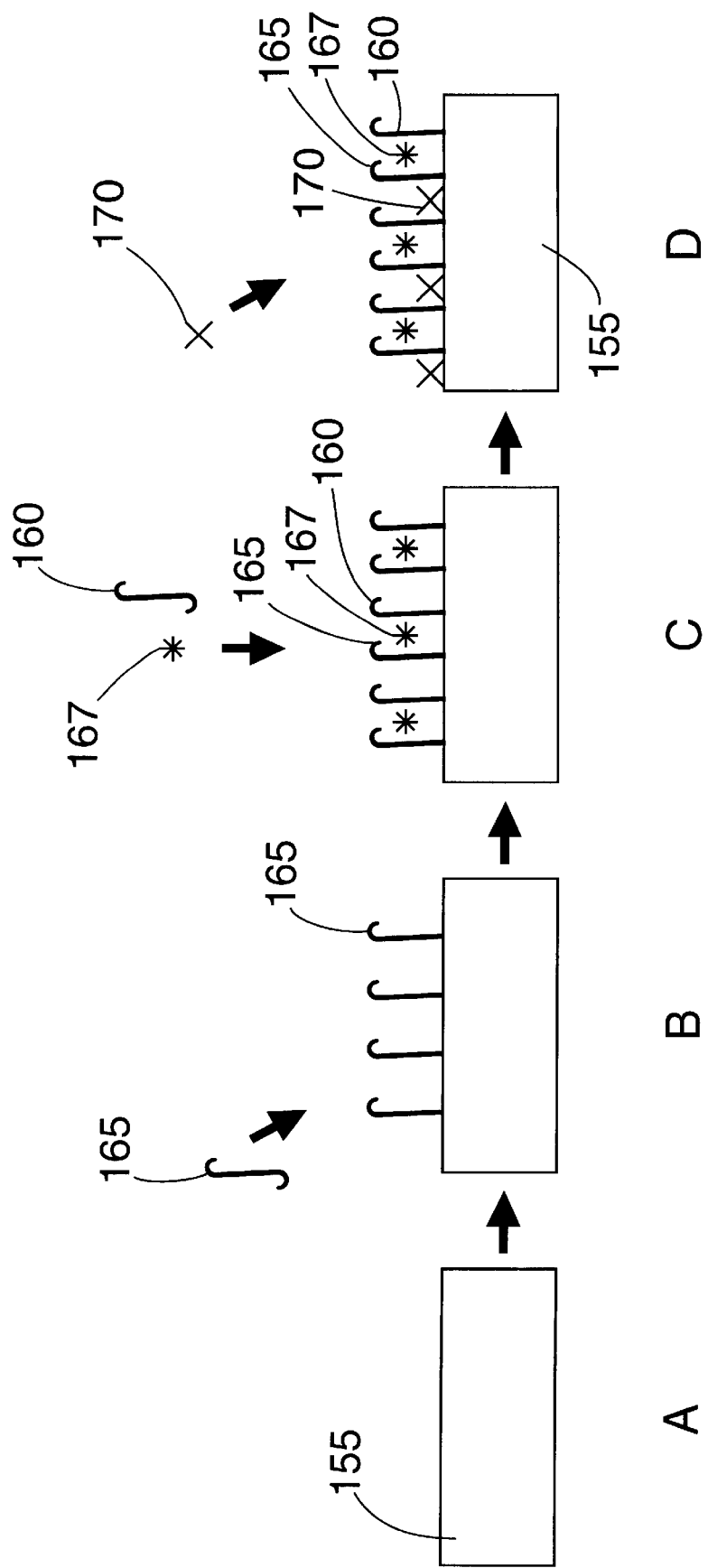
FIG. 3 shows another embodiment of the post hybridization activation method wherein the SER label is intercalated between the hybridized target oligonucleotide strand and the oligonucleotide gene probe strand.
Figure 4:
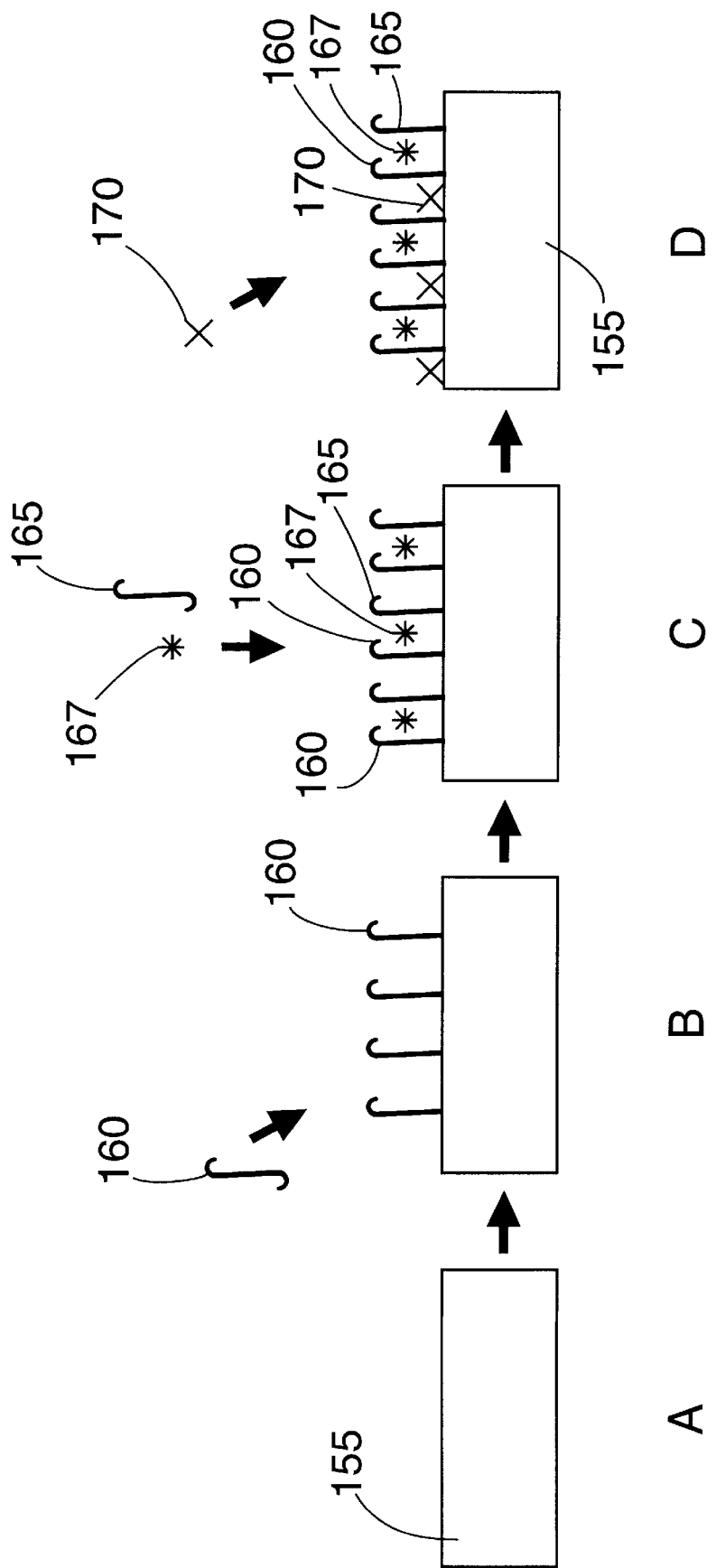
FIG. 4 shows yet another embodiment of the post hybridization activation method wherein the SER label is intercalated between the hybridized target oligonucleotide strand and the oligonucleotide gene probe strand.

The SER label can be designed such that its Raman characteristics (e.g., intensity, frequency, polarization) changes depending upon whether a single oligonucleotide strand is labeled with the SER label or whether a hybridized double oligonucleotide strand is labeled with the SER label or whether the SER label is in an unbound free state. When using such a label, it is not necessary to bind the label to an oligonucleotide strand, but the SER label may be delivered as a free molecule. If hybridization occurs, these specially designed SER labels can be intercalated or entrapped in the double strand. If hybridization does not occur, then the SER label remains in a free state. The difference in the SERS detection of SERS signal characteristic between the free state and the intercalated or entrapped state of the SER label can be used as an indication of hybridization. FIG. 3 illustrates this embodiment wherein the SER label 167 is intercalated between the immobilized oligonucleotide probe 165 and the target oligonucleotide strand 160. If hybridization does not occur between the probe and a target oligonucleotide strand, then the SER label remains in the free state. Then, after hybridization, the support means is SER activated with a SER activating means 170. FIG. 4 simply illustrates an alternate method to FIG. 3 whereby the target oligonucleotide strand 160 is immobilized on the support means 155 before it is incubated with a solution containing SER labels 167 and oligonucleotide probes 165. If hybridization occurs between the immobilized target oligonucleotides 160 and the oligonucleotide probes 165, the SER label 167 is intercalated or entrapped between the two strands. If hybridization does not occur, then the SER label will remain in the free state. After hybridization, the support means 155 is SER activated with a SER activating means 170.

Because SER gene probes rely on chemical identification, rather than emission of radioactivity, they have a significant advantage over radioactive probes. SER gene probes are formed with stable chemicals which do not emit potentially dangerous ionizing radiation. Furthermore, the probes offer the excellent specificity inherent to Raman spectroscopy. While isotope labels are few, many chemicals can be used to label DNA for SERS detection. Potentially up to hundreds of different SER gene probes can be constructed. A large number of probes with different labels could be used to simultaneously probe one immobilized DNA, PNA or RNA of interest.

Figure 5:
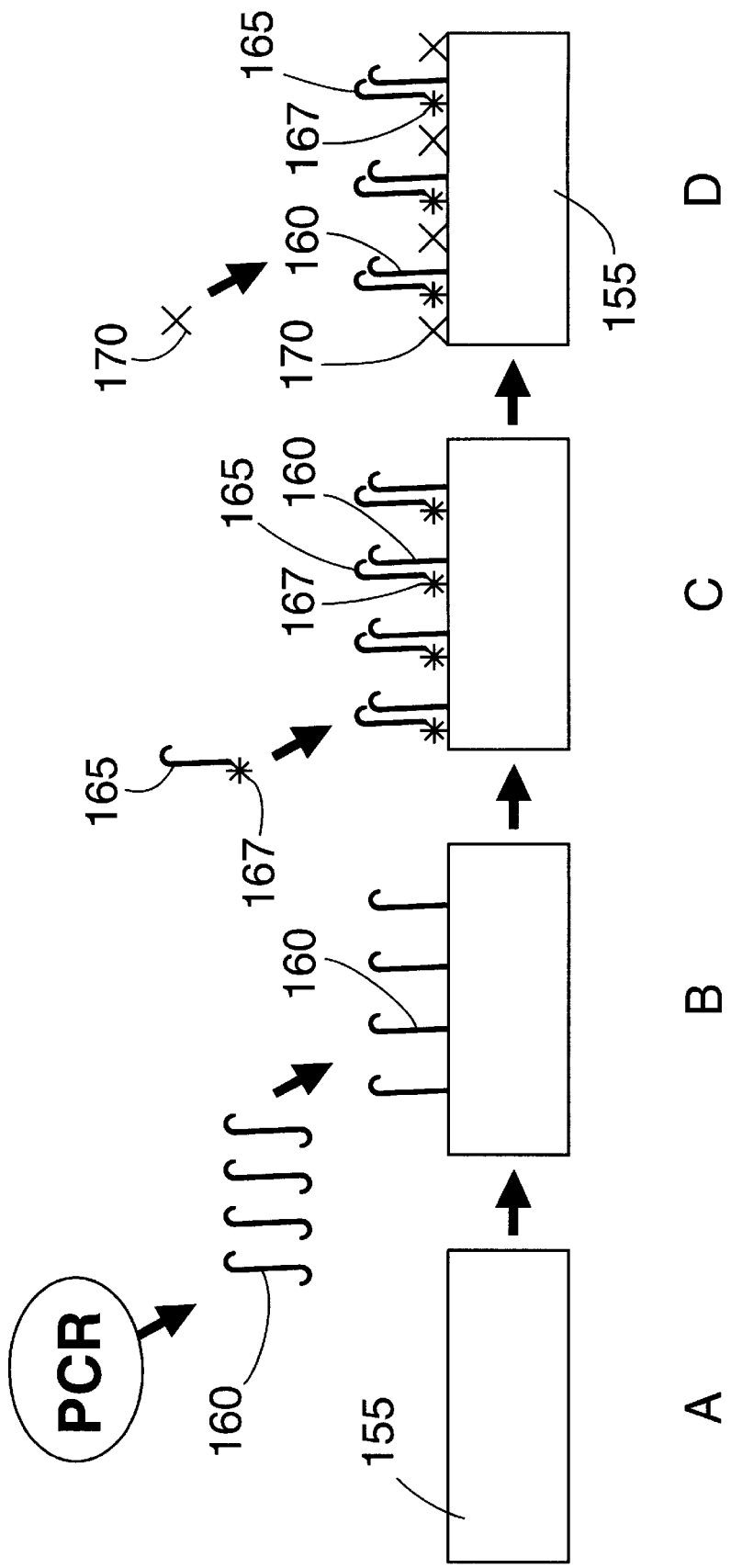
FIG. 5 shows another embodiment of the post hybridization activation method wherein PCR steps are performed to amplify target oligonucleotide strands labeled with a SER label.
Figure 6:
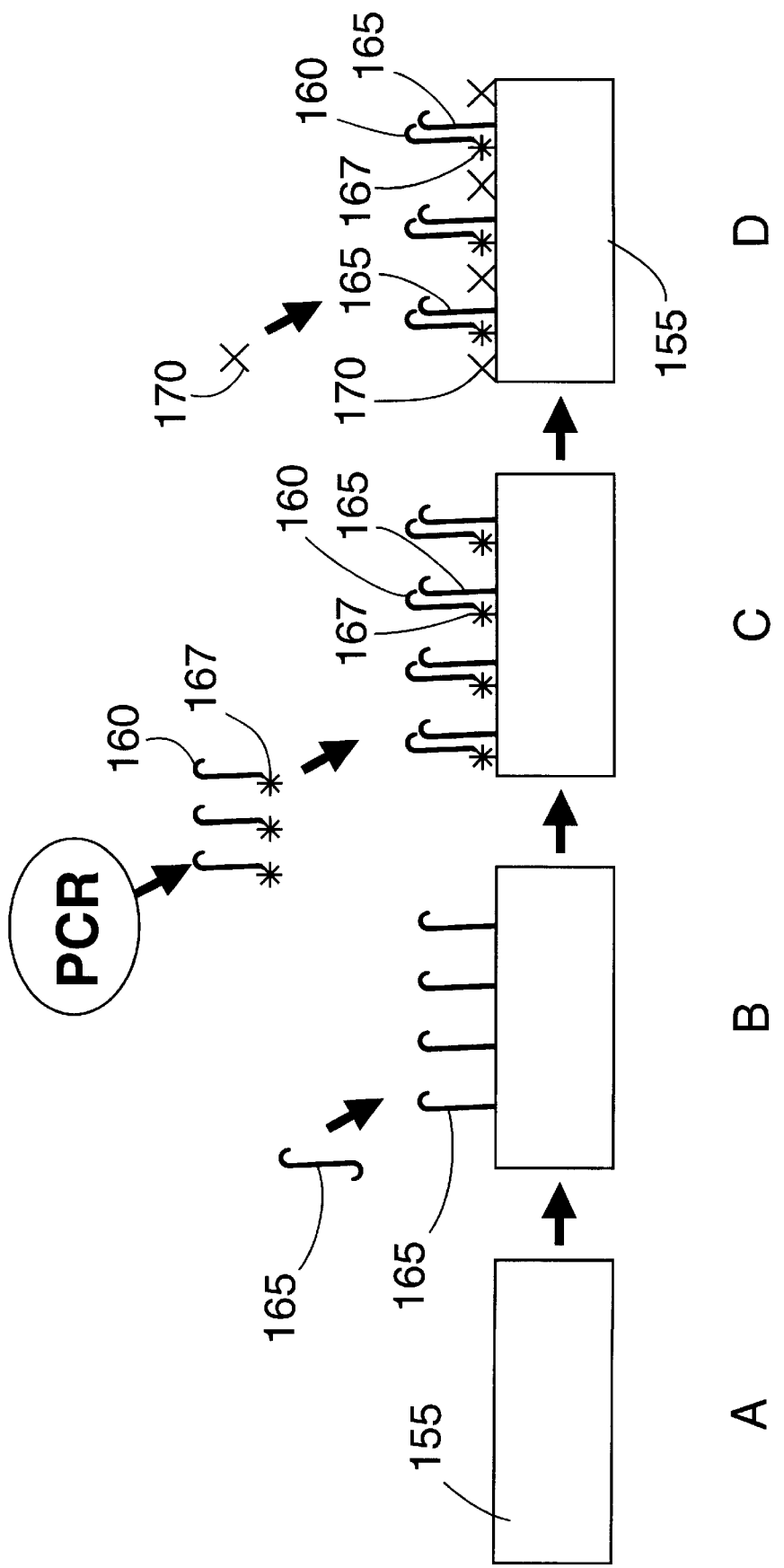
FIG. 6 shows another embodiment of the post hybridization activation method wherein PCR steps are performed to amplify the target oligonucleotide strands labeled with a SER label.

FIG. 5 and FIG. 6 illustrate that PCR steps can be performed to amplify the target region of the target oligonucleotide strands. FIG. 5 shows the target oligonucleotide 160, after amplification using PCR steps, are immobilized on the surface of the support means 155. Then the support means is incubated with a solution of oligonucleotide probes 165 labeled with a SER label 167. Then, the support means is SER activated by a SER activating means 170. FIG. 6 is an alternative to FIG. 5 whereby the gene probes 165 are first immobilized on the support means 155, then the support means is incubated in a solution of oligonucleotides of unknown sequence 160 taken from a target sample suspected of containing target oligonucleotides. Prior to incubation in step c of FIG. 6, the unknown oligonucleotides 160 are amplified using PCR steps and were labeled with a SER label 167. The support means 155 is incubated in the solution of SER-labeled unknown oligonucleotides for a time sufficient enough that the unknown oligonucleotides will contact the immobilized gene probes and hybridization between the immobilized gene probes and the SER-labeled target oligonucleotides will have time to take place. After hybridization, the support means is SERS activated by a SER activating means 170.

Figure 7:
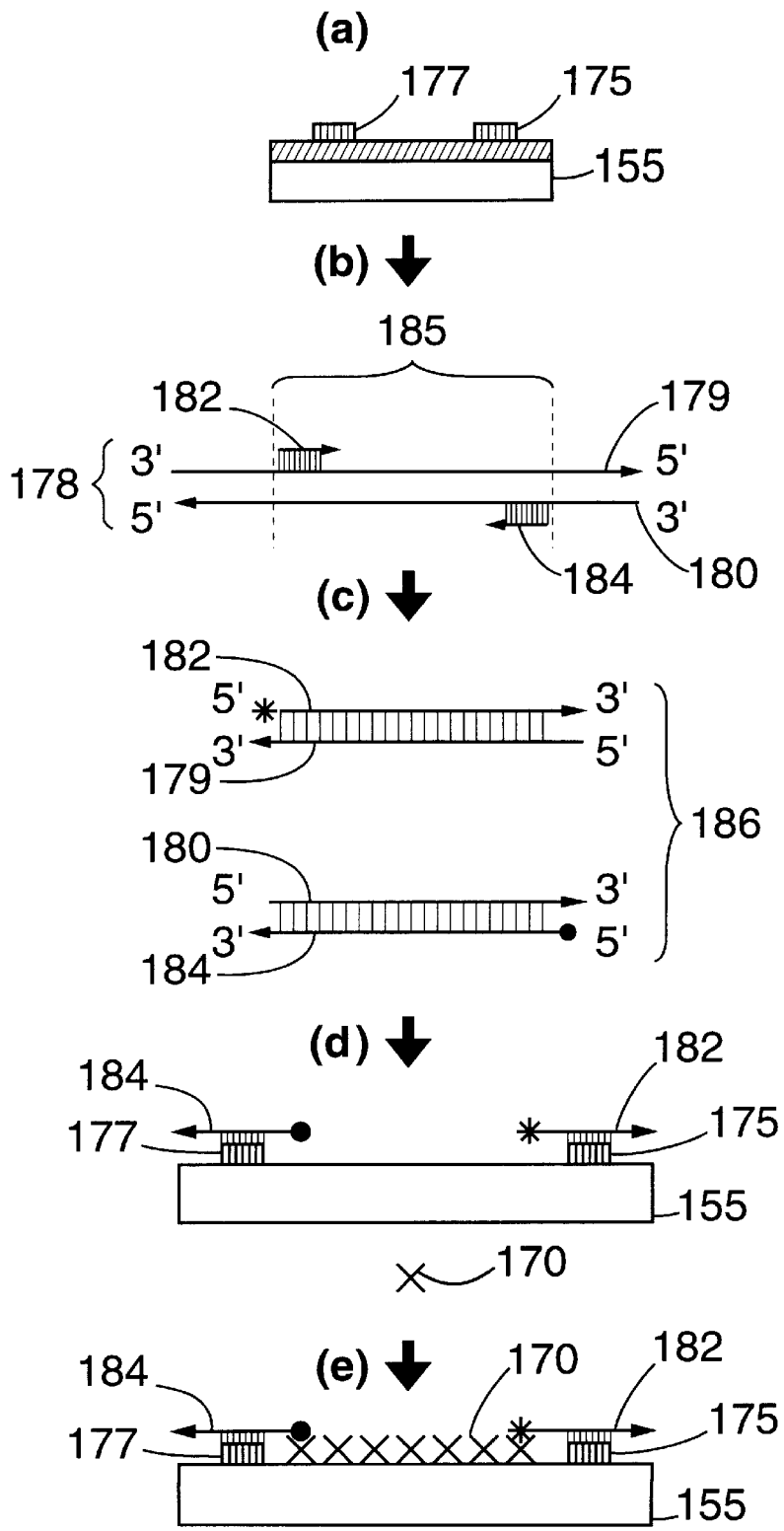
FIG. 7 illustrates a method for using SER-labeled primer in conjunction with Polymerase Chain Reaction to produce amplified SER-labeled target oligonucleotide strands.

FIG. 7 illustrates a method for using the SER gene probe in conjunction with polymerase chain reaction (PCR) to detect target DNA strands. PCR can be used to amplify the target regions of target oligonucleotides in conjunction with the PHA methods as illustrated in FIGS. 1–6 and described herein. PCR can also be used to amplify the target regions of target oligonucleotides in conjunction with the SHA methods as illustrated in FIGS. 8–13 and described below. In FIG. 7, unlabeled DNA strands of known sequences 175 and 177, complementary to the double-stranded target DNA 178, respectively, are adsorbed onto a support means 155 (step a, FIG. 7). The support means 155 is free of SERS activity initially. The SER-labeled gene probes 182 and 184 are synthesized and used as SER-labeled primers. One or two labeled primers can be used. In FIG. 7, these primers 182 and 184, of approximately 20 bases, are complementary to sites on the opposite DNA strands 179 and 180 on either side of the double-stranded target DNA 17& Note that each primer hybridizes to the opposite strand, whereby primer 182 hybridizes with strand 179 of the target DNA 178 and primer 184 hybridizes with strand 180 of the target DNA 17& Then, PCR is performed in the following manner: (step b) the DNA strands are isolated and denatured to form single-stranded templates (179 and 180) by heating to 90–95° C. for approximately 1 minute. The two primers 182 and 184 are annealed to the isolated single stranded DNA templates at 40–60° C. and then cooled for about 2 minutes and (step c) DNA polymerase (purified from the thermophilic bacterium *Thermus aquaticus*, Taq DNA polymerase) is added at about 72° C. for about 2 minutes, resulting in extension of the DNA molecule (amplification) through the target region 185 of the DNA strand 17& (Step d) Following amplification by PCR, the support means 155 is immersed and incubated in the sample containing the amplified products 186, which are the SER-labeled amplified DNA segments, for a sufficient time as for hybridization between the SER-labeled amplified DNA segments and the unlabeled DNA strands 175, 177 on the support means 155 to occur to completion and a SERS signal can be detected. The support means having the unlabeled DNA strands complementary to the target DNA strand will detect the SER-labeled amplified DNA segments. Following multiple cycles, there has been exponential amplification of the target region 185 containing SER-labeled primers 182 and 184. Therefore, the SER-labeled primers 182 and 184 have been amplified as well. This process can be repeated through any number of cycles to yield many copies of the target sequence.

Figure 8:
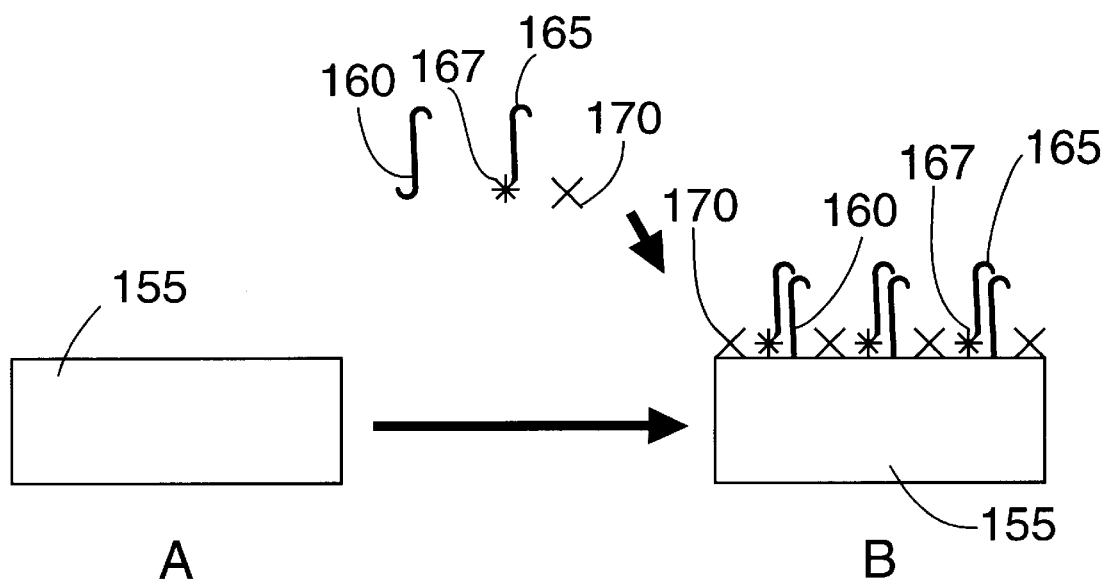
FIG. 8 shows one embodiment of the simultaneous hybridization activation method.
Figure 9:
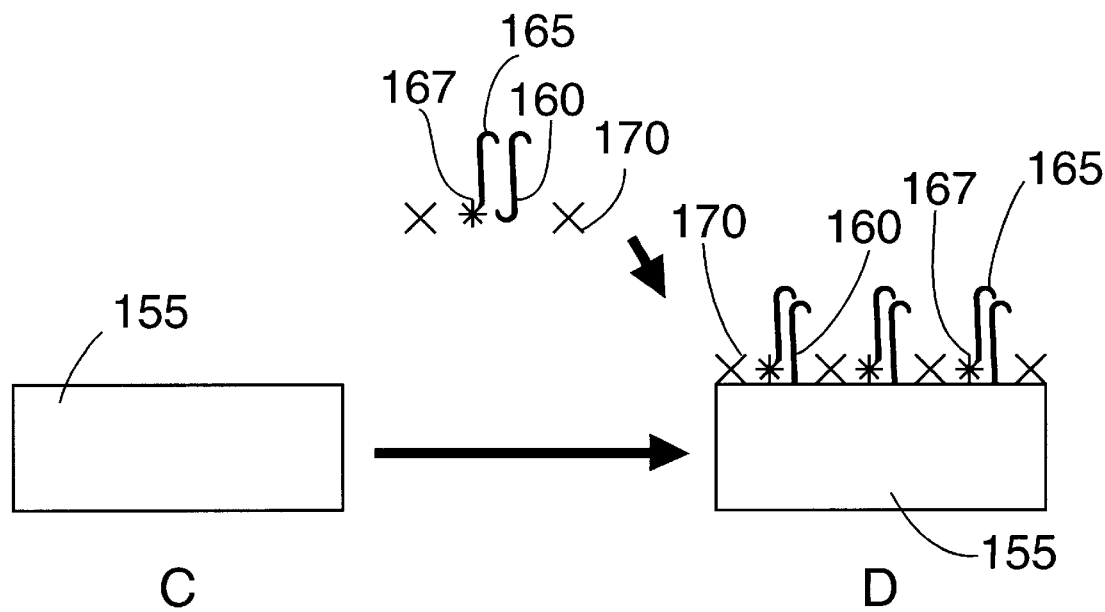
FIG. 9 shows another embodiment of the simultaneous hybridization activation method.

FIG. 8 illustrates an SHA method wherein the support means 155 is incubated for a sufficient period of time with a sufficient amount of solution comprising unknown oligonucleotide strands 160, gene probes 165 having a SER label 167 and a SER activating means 170 for a sufficient time so that the oligonucleotide strands 160 adsorb onto the support means 155 while simultaneously hybridizing with the SER-labeled gene probes 165 and while the support means is SER activated with the SER activating means 170 simultaneously with hybridization. A second embodiment of SHA is shown in Fi& 9 wherein the support means 155 is incubated for a sufficient time period in a sufficient amount of a solution comprising SER activating means 170 and SER-labeled hybridized oligonucleotide material comprising SER-labeled gene probes 165,167 hybridized with target oligonucleotides 160 for a period of time sufficient so that the SER-labeled hybridized oligonucleotide material adsorbs onto the support means 155 and the support means is SER activated simultaneously.

Figure 10:
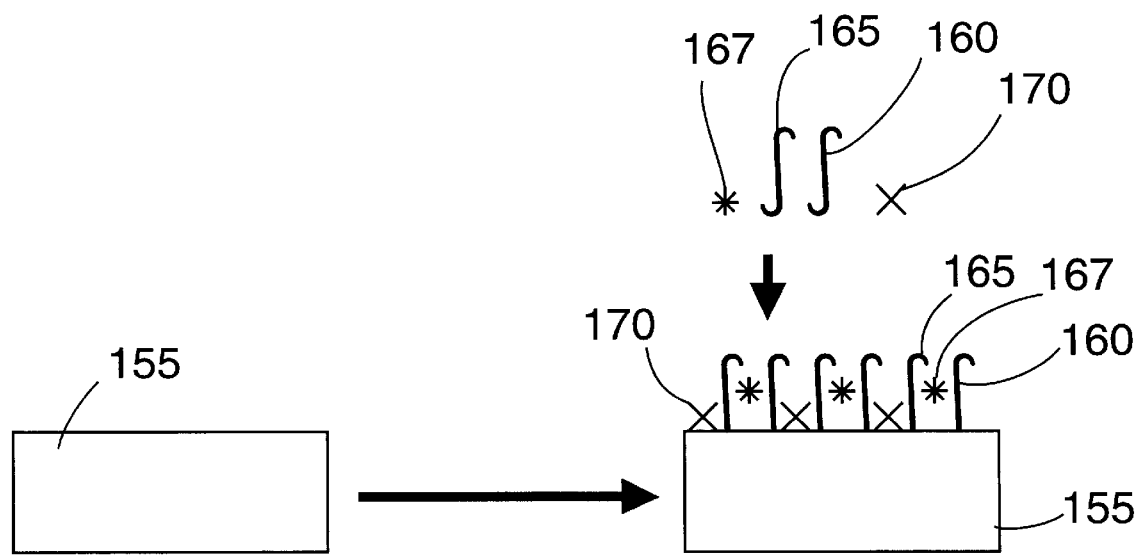
FIG. 10 shows yet another embodiment of the simultaneous hybridization activation method wherein the SER label is intercalated between the hybridized target oligonucleotide strand and the oligonucleotide gene probe strand.
Figure 11:
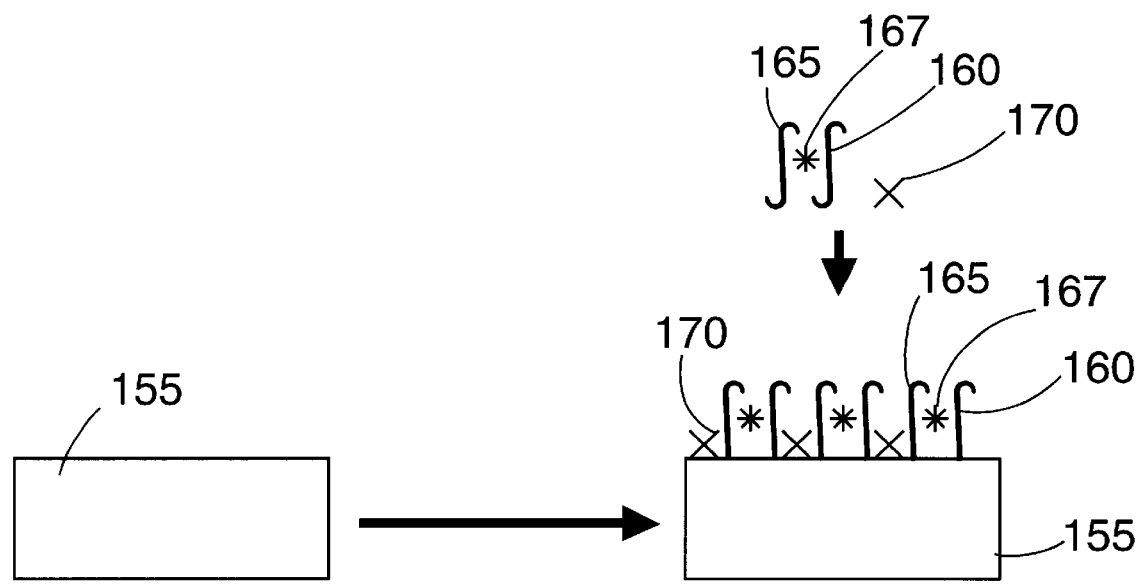
FIG. 11 shows another embodiment of the simultaneous hybridization activation method wherein the SER label is intercalated between the hybridized target oligonucleotide strand and the oligonucleotide gene probe strand

FIG. 10 shows another method wherein the support means 155 is incubated for a sufficient period of time in a sufficient amount of solution comprising SER activating means 170, SER labels 167 in the free state, gene probes 165 and unknown oligonucleotides 160 for a period of time sufficient enough so that the gene probes 165 hybridize with the target oligonucleotides 160 and the SERS label 167 is intercalated between the oligonucleotide probe 165 and the target oligonucleotide strand 160, while simultaneously along with hybridization, the target oligonucleotides 160 and the oligonucleotide probe 165 is adsorbed onto the support means 155 and the support means is SER activated by the SER activating means 170. If hybridization does not occur between the gene probe and a target oligonucleotide strand, then the SER label remains in the free state. FIG. 11 shows yet another method whereby the support means 155 is incubated for a sufficient period of time with a sufficient amount of solution comprising a SERS activating means 170 and SERS-labeled hybridized oligonucleotide material comprising a target oligonucleotide 160 hybridized with a gene probe 165 with a SER label 167 intercalated between the two oligonucleotide strands. The support means is incubated with the solution for a period of time sufficient so that the SER-labeled hybridized material is adsorbed onto the support means 155 while simultaneously the support means is SER activated by the SER activating means 170.

Figure 12:
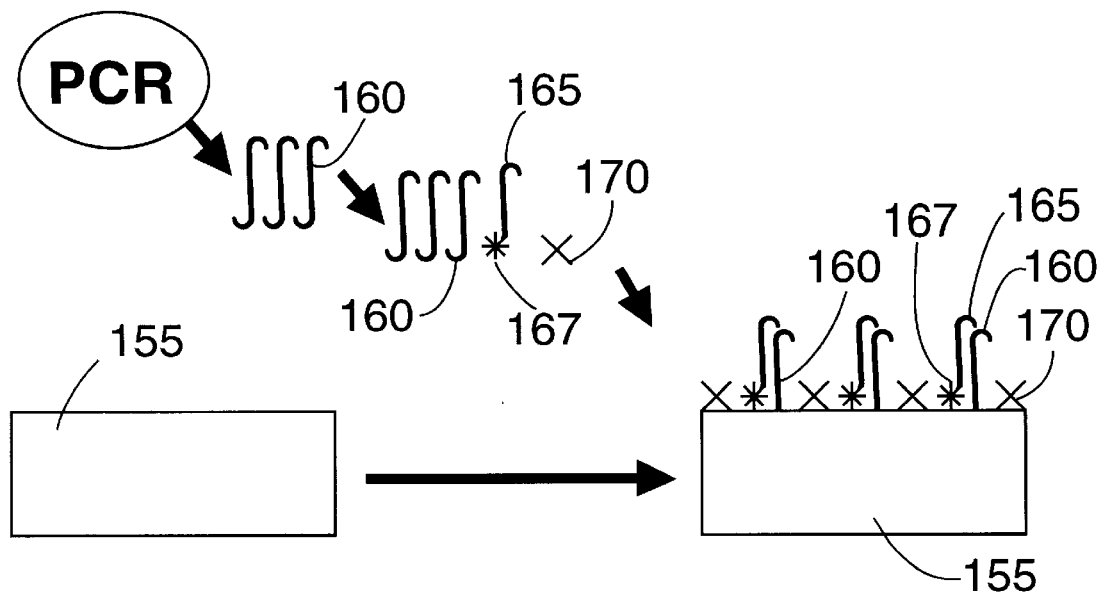
FIG. 12 shows another embodiment of the simultaneous hybridization activation method wherein PCR steps are performed to amplify target oligonucleotide strands labeled with a SER label.
Figure 13:
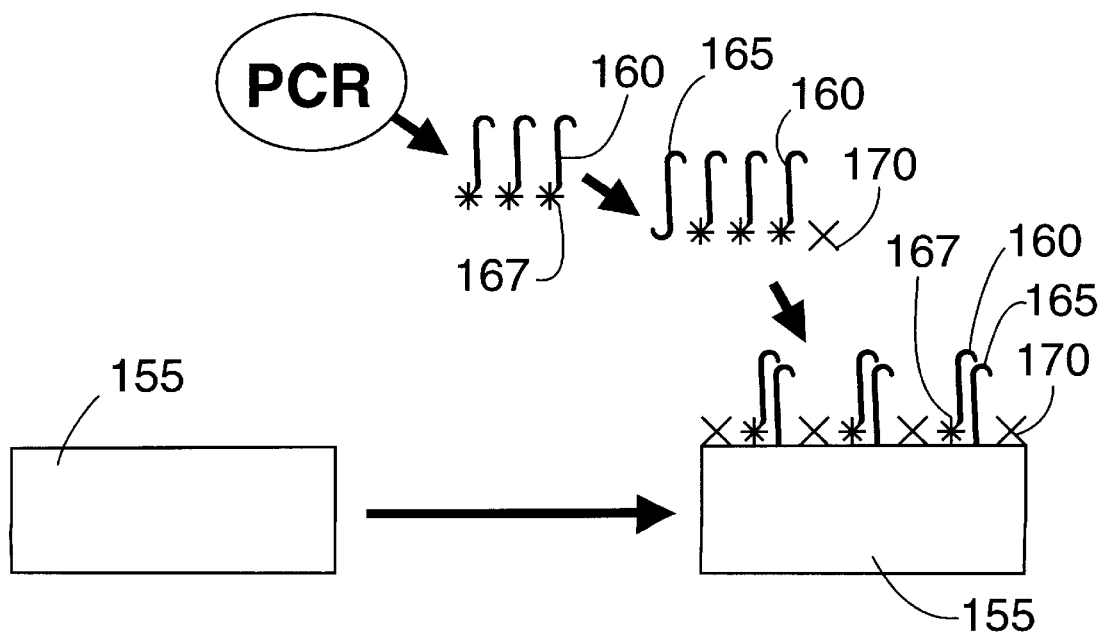
FIG. 13 shows another embodiment of the simultaneous hybridization activation method wherein PCR steps are performed to amplify the target oligonucleotide strands labeled with a SER label.

Both embodiments of SHA can be performed in conjunction with PCR steps for amplification of the target oligonucleotide strands or without PCR steps if the detection sensitivity is sufficient. FIG. 12 shows that PCR can be done to amplify target oligonucleotides 160 for the SHA method wherein the amplified target oligonucleotides 160 are in solution with gene probes 165 having a SER label 167 attached thereto and a SER activating means 170. When the support means 155 is incubated with the solution, hybridization occurs between the target oligonucleotides 160 and the SER-labeled gene probes 165,167 occurring at the same time as adsorption onto the surface of the support means 155 and at the same time as the support means 155 being SER activated by the SER activating means 170. FIG. 13 again shows that PCR steps can be performed to amplify target oligonucleotides 160 that are labeled with SER labels 167 for the SHA method wherein the amplified SER-labeled target oligonucleotides are in solution with gene probe oligonucleotides 165 and SER activating means 170. When the support means 155 is incubated with the solution, hybridization occurs between the SER-labeled target oligonucleotides and the gene probes occurring at the same time as adsorption onto the surface of the support means and at the same time as the support means being SER activated by the SER activating means.

One method of simultaneous hybridization activation involves SER activation of the substrate being induced by coating the sample substrate or post-PCR sample substrate with 100 Å silver. Silver deposition can be performed via thermal evaporation at approximately $2\times10^6$ Torr in a vacuum evaporation system (such as Cooke Vacuum, CV 301) at a deposition rate of 0.3–0.5 Å/second. Both PHA and SHA methods can take advantage of the PCR method to amplify the target DNA as well as the use of the amplified target DNA with a SER-active label. There are several alternatives for inducing the SERS effect in gene probe detection.

The SER gene probe 165,167, as shown in the figures, has at least one oligonucleotide strand 165, as shown in the figures, labeled with at least one SER label 167, as shown in figures. Oligonucleotides include DNA, RNA and PNA. The oligonucleotide of the SER gene probe either has the SER label attached to the strand or if two oligonucleotide strands are used, the SER label can be intercalated between the two oligonucleotide strands, enveloped by the oligonucleotide strands holding the label in place. If the SER label is attached to the oligonucleotide strand, the label can be attached either at the end of the strand or at any site between the strand ends. More than one SER label can be used to label as long as it does not interfere with hybridization.

The oligonucleotide strand of the SER gene probe is of known sequence and is complementary to a target oligonucleotide strand that may be immobilized on the support means. If the target oligonucleotide strand is present in the test sample, and it is immobilized on the support means, then hybridization between the target oligonucleotide strand and the SER gene probe will occur and the hybridization will be detected. Alternatively, the oligonucleotide strand of the SER gene probe is of unknown sequence and the immobilized oligonucleotide on the support means is complementary to the target oligonucleotide. The unknown oligonucleotide strand of the SER gene probe may or may not be the target oligonucleotide. If it is the target oligonucleotide then it will hybridize with the complementary immobilized oligonucleotide adsorbed on the support means. The SER label is unique for a particular target oligonucleotide of a particular sequence that is characteristic of a particular bacteria, virus or genetic material. So, if there are more than one SER gene probe utilized to assay for more than one particular oligonucleotide sequence characteristic of a particular bacteria or virus, then each SER gene probe that is unique for a particular target oligonucleotide strand will have a different, separate unique SER label. Target oligonucleotide strands in a multiple assay having the same sequence are designated for the same SER label. The label is a specific chemical group that can be detected using the SERS spectrographic technique.

Other procedures for SER activation of a substrate include: (1) delivering onto the substrate a colloidal solution of silver nanoparticle hydrosol; (2) spraying reagents to form silver sols onto the substrates; (3) chemical deposition and any other means for SER activation.

Colloidal solutions of metal such as silver can produce nanoparticles that enhance the Raman signal. Silver colloid hydrosols are often used to produce SER-active media in solutions. In the present invention, hybridization is first performed on a solid substrate, then the substrate is covered by a silver (or gold) nanoparticle solution. This procedure is easily implemented with current hybridization schemes. Silver colloids are generally prepared by rapidly mixing a solution of $AgNO_3$ with ice-cold $NaBH_4$ or sodium citrate. The sols are made with sodium citrate and silver nitrate or sodium borohydride and silver nitrate. The methods are quite different because of the differences in the reducing potential of the two reductants. The borohydride is added batchwise over an hour to an ice-cold solution of silver nitrate with polyvinyl alcohol (PVA) added during the process to a final concentration of 1%. The final solution is boiled for one hour to destroy any remaining borohydride. The procedure implementing the PVA additive is used to produce silver sol solutions that are still active several months after preparation. Gold and silver colloids have been investigated as SER-active media for various dyes.

Metal colloid hydrosols are often used to produce SER-active media in solutions. There are several reasons for using colloid hydrosols including ease of colloid formation and straightforward characterization of the colloid solutions by simple UV absorption. For example, silver colloids are generally prepared by rapidly mixing a solution of $AgNO_3$ with ice-cold $NaBH_4$. Colloid systems tend to coagulate making them not very stable and difficult to use. Stabilizers such as poly(vinylalcohol), poly(vinylpyrrolidone) and sodium dodecyl sulfate have been used to minimize this coagulation problem. Silver colloids can be stabilized by filter paper or membrane supports (cellulose, glass, nylon, Teflon™, and quartz fibers) could enhance the Raman emission. Colloid silver hydrosols can provide efficient media for SERS measurements for the SER gene probe. An attribute of this technique using silver hydrosols is that it does not require the use of evaporation vacuum chambers. The main advantage of the colloid SERS technique is the relatively simple experimental procedures for preparation of the hydrosol solutions. Measurements with the colloid hydrosols indicated that for carefully prepared samples, the unaggregated colloids were stable for periods of more than 3 weeks.

Another method of delivering metal sol onto the support means having hybridized products with SER-active labels is by spraying reagents onto the substrate to form nanoparticles of metal sols such as silver or gold. In this method, reagents to form silver sols are delivered onto the substrates where hybridization has taken place, and the formation of nanoparticle silver sols can occur in situ on the substrate. Other alternative methods includes chemical deposition as described by Y. S. Li et al in *Appl. Spectros.*, vol. 46 (1992), pp. 1354–1357. Another alternative method includes binding silver onto treated surfaces of glass or other materials (e.g., thiols groups on surface can bind silver). Another alternative method includes physical deposition wherein silver nanoparticles is physically deposited onto the substrate. In addition, an electrochemical method can also be used wherein an electrochemical reaction is induced to roughen the substrate surface (e.g., electrode) on which the hybridization had taken place. The roughening process is the SER activation procedure.

A silver or gold staining method can also be used which has been used for permanent staining of proteins or nucleic acid in gels (e.g., polyacrylamide gels). In silver staining, gels are impregnated with soluble silver ions ($Ag^+$) and developed by treatment with a reductant. Macromolecules in the gel promote the reduction of silver ion to metallic silver, which is insoluble and visible, allowing protein- or nucleic acid-containing materials to be seen. In the SER gene method, the metallic silver are made to form nanoparticles of metallic silver, which can be used to enhance the Raman signal.

Yet another means for SER activation of the support means includes the use of hybridization between target oligonucleotides and complementary gene probe oligonucleotides (wherein the SER label is either attached to the target oligonucleotide or to the gene probe or the SER label is intercalated between the two hybridized oligonucleotide strands) on nanobeads or nanoparticles, then the nanobeads are transferred to a support means, then the support means is SER activated. The nanobeads or nanoparticles are made of polystyrene, glass, silica or other material suitable for DNA or oligonucleotide binding. In this procedure, the metal coated nanobeads provide submicron roughness for SERS activation of the support means following the activation process. In another embodiment, the nanobeads are magnetic nanoparticles that can be transferred to other support means using magnetic fields.

The method of SER activation of the support means can incorporate a blotting procedure such as the Southern blotting technique, the Western blotting technique or the Northern blotting technique. A blotting technique provides an alternate method of recovering the hybridized oligonucleotide material from the nitrocellulose filter and transferring combined into one step, by simply blotting the hybridized oligonucleotide material directly onto the SER-active support means. The small amount needed to be transferred onto the support means is an amount sufficient enough as to provide a detectable quantity of hybridized oligonucleotide material to the SER-active support means. PCR procedures can also be used before the blotting procedure is performed.

Figure 14:
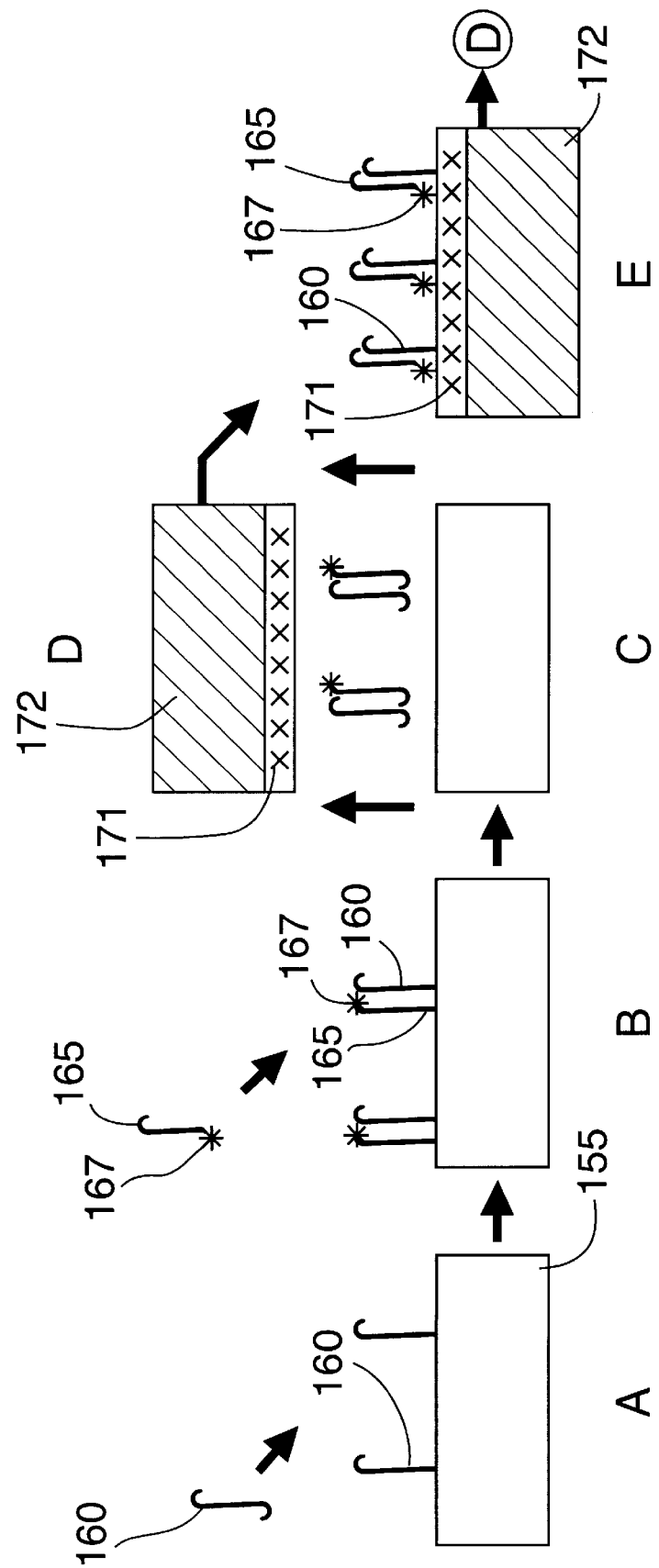
FIG. 14 shows another embodiment of the post hybridization activation method wherein the immobilized SER-labeled hybridized oligonucleotide material is transferred from a nonSER-active support means to a SER-active blot for detection and analysis.
Figure 15:
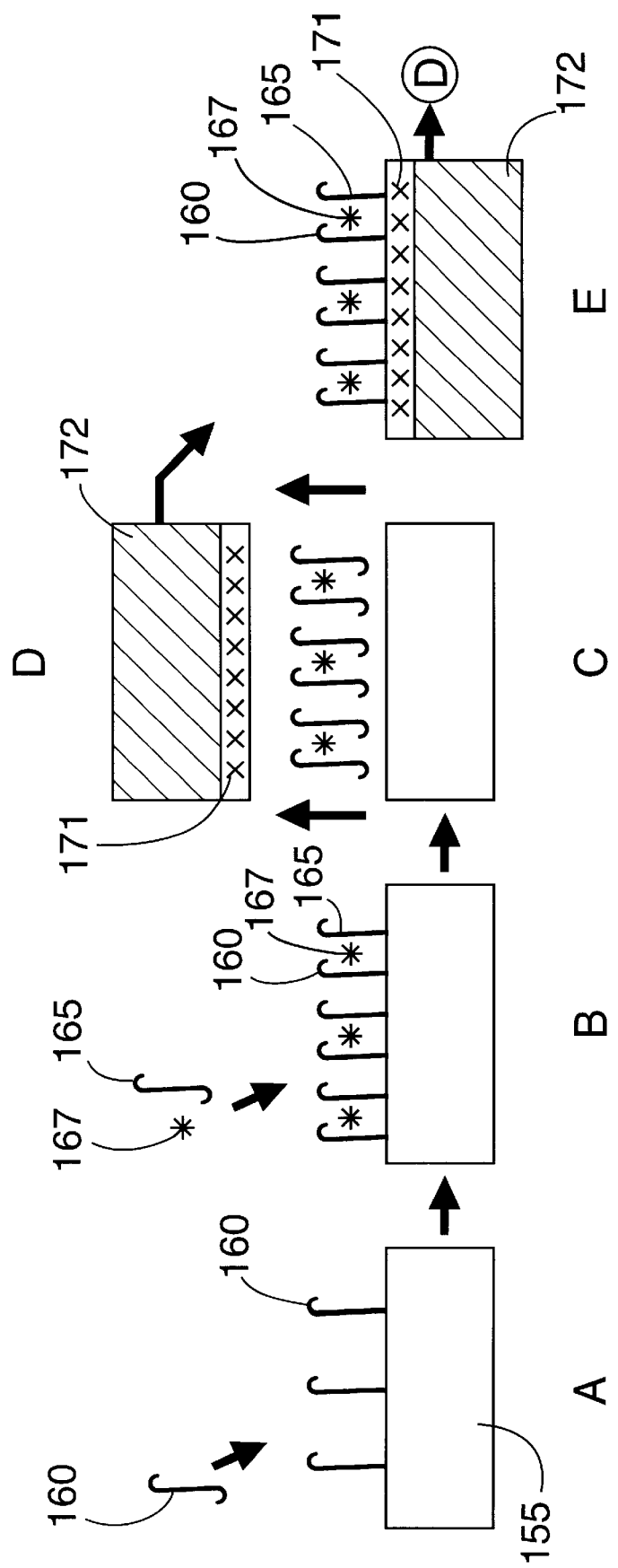
FIG. 15 shows another embodiment of the post hybridization activation method wherein the immobilized hybridized oligonucleotide material having the SER label intercalated between the two hybridized oligonucleotide strands is transferred from a nonSER-active support means to a SER-active blot for detection and analysis.

One way the blotting procedure can be performed is by applying an electric field to absorb the SER-labeled hybridized oligonucleotide material onto a SER-active blot, as illustrated in FIG. 14. FIG. 14 shows the method wherein the SER-labeled hybridized oligonucleotide material, comprising the immobilized target oligonucleotide 160 hybridized with the SER-labeled gene probe 165,167, is transferred from the nonSER-active support means 155 to a SER-active blot 172 wherein the SER-active blot 172 has a metal layer 171 that has an applied voltage. Thus, the transfer takes place wherein the SER-labeled hybridized oligonucleotide material which is initially immobilized on the support means 155, having no SERS activity, is adsorbed onto the SER-active blot 172 for detection and analysis. Thus, this procedure increases adsorption and better transfer. This procedure is often used in electroblotting and is most suitable for DNA products that have electrical charge. FIG. 15 shows an alternate embodiment of the method illustrated in FIG. 14 wherein the support means 155, having immobilized unknown oligonucleotide strands 160 adsorbed thereon, is incubated for a sufficient period of time with a solution comprising known gene probes 165 and SER labels 167 in the free state, incubated for a period of time sufficient so that hybridization will take place between the immobilized target oligonucleotides 160 and the gene probes 165 with the SER label 167 being intercalated or entrapped between the two oligonucleotide strands. The immobilized SER-labeled hybridized oligonucleotide material is transferred from the nonSER-active support means 155 to a SER-active blot 172 wherein the SER-active blot 172 has a metal layer 171 that has an applied voltage. Thus, the transfer takes place wherein the SER-labeled hybridized oligonucleotide material which is initially immobilized on the support means 155, having no SERS activity, is adsorbed onto the SERS-active blot 172 for detection and analysis.

An alternate embodiment of the SER-active blot 172 in both FIG. 14 and 15 includes a metal electrode surface. Electrochemical cells using metal electrodes such as silver can be used for SERS. Silver at the electrode is oxidized by the reaction $Ag \rightarrow Ag^+e^-$ during the first half of the cycle. During the reduction half cycle, a roughened silver or metal surface is reproduced by the reaction $Ag^+ + e^- \rightarrow Ag$. This oxidation-reduction procedure generally produces surface protrusions in the size range of 25–500 nm on the electrode surface. The working electrode is generally placed in a position such that the laser excitation can be focused onto its surface and the Raman scattered light can be efficiently collected by appropriate optics. Strong SERS signals appear only after an electrochemical oxidation-reduction cycle (the activation cycle) is performed on the metal electrode. Other metal electrodes such as platinum, gold and copper can also be used.

Figure 16:
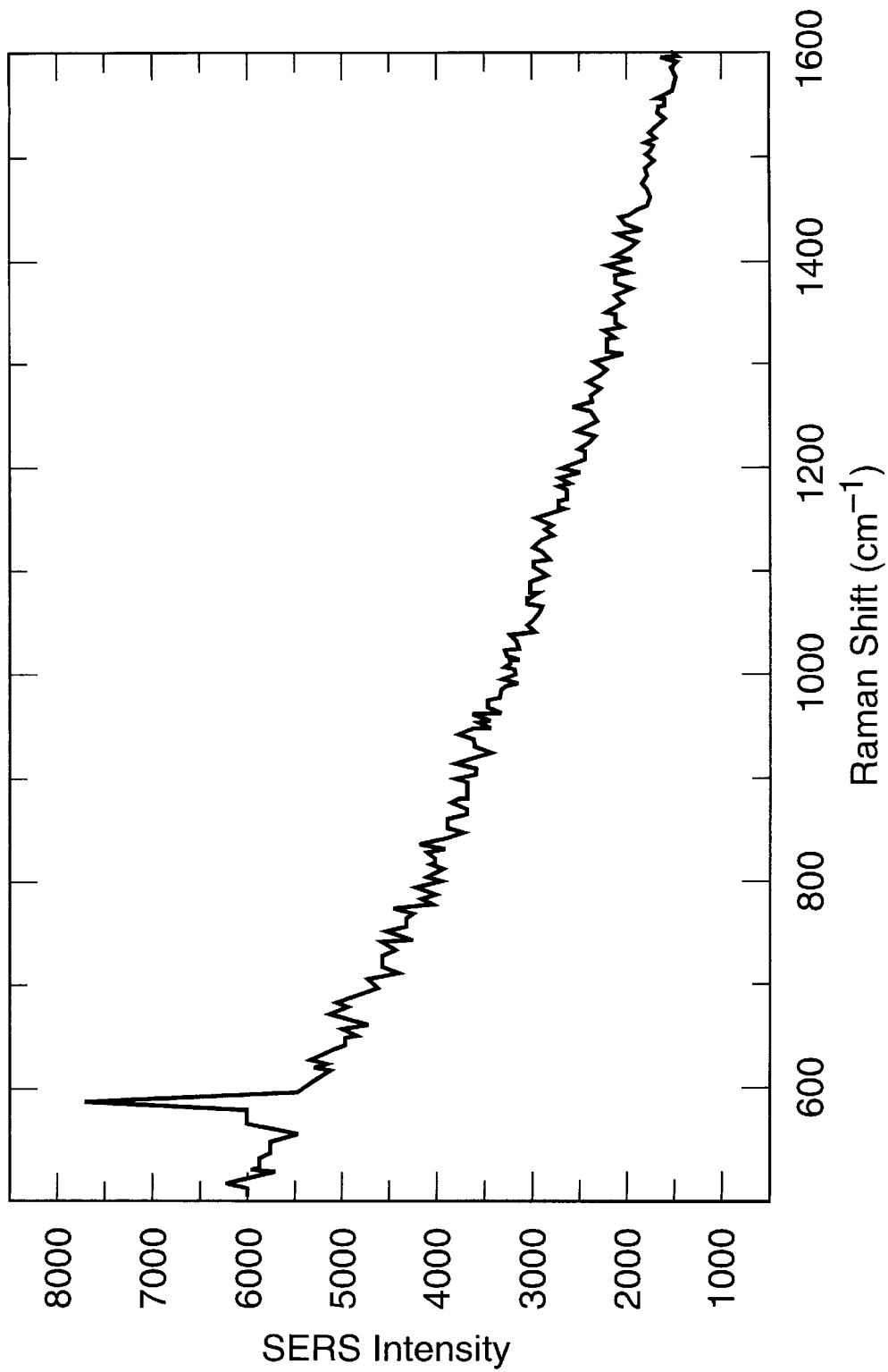
FIG. 16 is a SERS spectrum of CFV-labeled DNA hybridized on a plastic-backed nitrocellulose substrate.

The methods and systems described in Applicant's application opens the possibility for extending the SER gene probe technology to many existing DNA assays that use hybridization substrates suitable for hybridization to occur on its surface, membranes that are suitable for hybridization to occur or blotting materials. For instance, there are many commercial membranes such as nylon membranes, nitrocellulose membranes, etc. FIG. 16 shows a SERS spectrum of CFV-labeled DNA hybridized on a plastic-backed nitrocellulose substrate with a 750 Å silver overlayer. The surface of the nitrocellulose substrate provides the submicron roughness needed to induce the SERS effect. The method comprised performing the hybridization on a nitrocellulose substrate, then it was washed thoroughly as described in Applicant's previous parent application, incorporated herein by reference. Then the substrate was coated with 750 Å silver, then it was analyzed. The silver coating was prepared by depositing 750 Å silver over the CFV-labeled DNA hybridization via vacuum evaporation system at approximately $2 \times 10^{-6}$ Torr (such as Cooke Vacuum, CV 301) at a deposition rate of 0.3–0.5 Å/second. The laser excitation used was the 647.1 nm emission line of a krypton laser (Coherent, Innova 70) at an excitation power of approximately 10 mW. The spectrum of the CFV-labeled DNA shows the sharp peak at 585 $cm^{-1}$. The post-hybridization approach has also been successfully demonstrated using silver sol delivery onto membranes where DNA hybridization has taken place.

Another method for SERS activation includes applying a thin film (e.g. 100 Å, less than 10 nm thickness) of a metal such as silver directly onto a support means. Under these conditions, the metal layer forms nanoparticles on the support means in the form of isolated metal islands. Upon increase of the deposited silver thickness, the particles would start to coalesce and form a continuous film. The size and shape of the metal nanoparticles can be influenced by varying the thickness of metal deposited (as measured by a quartz crystal monitor perpendicular to the evaporation source). In this method, with the use of metal nanoparticle island thin film, the roughness of the support means is not required to induce the SERS effect.

Other examples of various types of support means where hybridization takes place includes various metallic nanostructures such as the nanoparticle island thin film comprising base materials such as silver and other metals previously mentioned. Other examples are listed below in Table 1:

TABLE 1

Several Types of metallic nanostructures used for SERS

| Structures | Base Materials |
|---|---|
| Metal islands | Silver, other metals |
| Metal-coated nanospheres | Teflon, latex, polymer nanospheres |
| Metal-coated nanoparticles | Alumina, fumed silica, titanium oxide, |

TABLE 1-continued

Several Types of metallic nanostructures used for SERS

| Structures | Base Materials |
|---|---|
| | other oxides |
| Metal-coated surfaces | Cellulose, silica gel, polystyrene |
| Metal-coated etched quartz | Quartz |
| Metal-coated gratings | Crossed gratings, lithographic structures |
| Metal membranes | Silver membranes, other metals |
| Chemically etched metal | Metal |
| Physically roughened surfaces | Quartz, metal |

Target oligonucleotides or gene probes can be adsorbed on the surface of these nanostructures, then hybridization can occur on the surface of the nanostructure, then the surface is metal-coated by a SER activating means to SER-activated the support means. One example of this methodology includes if the oligonucleotides adsorb onto the surface of a nanosphere or a nanoparticle and hybridization occurs, the nanospheres or nanoparticles containing the SER-labeled hybridized target oligonucleotide material can be moved or transferred to a different support means wherein the nanospheres or nanoparticles coat the surface of the support means, then a layer of metal is disposed on the support means to coat the support means as well as the nanospheres or nanoparticles on its surface.

Preparation of nanosphere substrates involve delivery of a 50-$\mu$l volume of a suspension of latex or Teflon nanospheres onto the surface of a support means. The different types of support means includes filter paper, cellulosic membranes, glass plates, or quartz materials. The support means is then placed on a high-speed spinning device and spun at 800–2000 rpm for about 20 seconds. The spheres adhere to the support means' surface, providing uniform coverage. After hybridization occurs, the metal is then deposited on the nanosphere-coated support means in a vacuum evaporator at a deposition rate of 0.15–0.2 nm/s. The thickness of the silver layer deposited is generally 50–100 nm. The morphology of the surface (e.g., density of the nanostructures) can be influenced by varying the concentration of nanospheres in the aqueous suspension solutions prior to spin coating.

Nanoparticles with irregular shapes can also be used instead of regularly shaped nanospheres to spin-coat support means. For instance, alumina appears to be one of the most efficient materials for the production of SER-activated support means. The alumina surface consists of randomly distributed surface agglomerates and protrusions in the 10–100 nm range. These structures produce large electromagnetic fields on the surface when the incident photon energy is in resonance with the localized surface plasmons.

Titanium dioxide is an alternative material that can be used to produce the nanostructure roughness when coated on surfaces. The procedure to prepare these support means is similar to that used for nanospheres and alumina particles. Titanium dioxide materials are first deposited on glass and cellulose support means and then coated with a 50–100 nm layer of silver by thermal evaporation. Prior to deposition, titanium dioxide is prepared as a suspension in water (10% concentration by weight). The silver-coated titanium oxide surfaces obtained by this method provide efficient SER-active support means.

Another alternative material that can be used for the support means comprises a fumed silica-based support means. The fumed silica particles are suspended in a 10% water solution and coated onto a glass plate or filter paper. The substrate is then coated with a 50–100 nm layer of silver by thermal evaporation. With this type of support means, the fumed silica material, which has nanosized structures, provides the rough-surface effect for the SERS process. Hybridization is performed prior to SERS activation.

Another means of SERS activating a support means is by using lithographic techniques to produce controlled surface roughness. These surfaces of these support means consist of uniform arrays of isolated silver nanoparticles which are uniform in shape and size. These surfaces produce a Raman enhancement in the order of $10^7$ and have been used to test the electromagnetic model fo SERS.

Another type of support means is the use of etched quartz posts. The procedure using etched quartz posts utilizes an island film as an etch mask on a $SiO_2$ support means. The preparation of $SiO_2$ prolate posts is a multi-step operation that involves plasma etching of $SiO_2$ with a silver island film as an etch mask Since fused quartz is etched much more slowly than is thermally deposited quartz, a 500-nm layer of $SiO_2$ is first thermally evaporated onto fused quartz at a rate of 0.1–0.2 nm/sec. The resulting crystalline quartz is annealed to the fused quartz for 45 min at approximately 950° C. A 5 nm silver layer is then evaporated onto the thermal $SiO_2$ layer and the support means is flash-heated for 20 seconds at 500° C. This heating causes the thin silver layer to bead up into small globules, which act as etch masks. The support means is then etched for 30–60 minutes in a $CHF_3$ plasma to produce submicrometer prolate $SiO_2$ posts, which are then coated with a continuous 80 nm silver layer at normal evaporation angle. Another method consists of varying the angle of evaporation in order to produce silver nanoparticles on the tips of the quartz posts. The alumina and nanosphere-based support means are generally simpler to prepare than the quartz posts since they do not require silver mask deposition and plasma etching operations.

After hybridization, direct metal coating of special filter papers coated with silver also provide useful support means. One of the simplest types of support means is the silver membrane used for air particulate sampling. The filter already has micropores and interstices that provide the roughness features required to induce SERS. Chemical etching procedures can also be used as a SERS activating means. In one procedure, copper foil is etched for 40 min. with $Al_2O_3$ at 4 bar pressure and subsequently etching for 2 minutes. Hybridization is done prior to the etching process.

A variety of methods can be used to enhance the detection of DNA probe using SERS. These methods consist of adding reagents that enhance the binding of nucleic acids onto silver. A variety of these reagents have been used in DNA analysis, such as spermine and spermidine.

Figure 17:
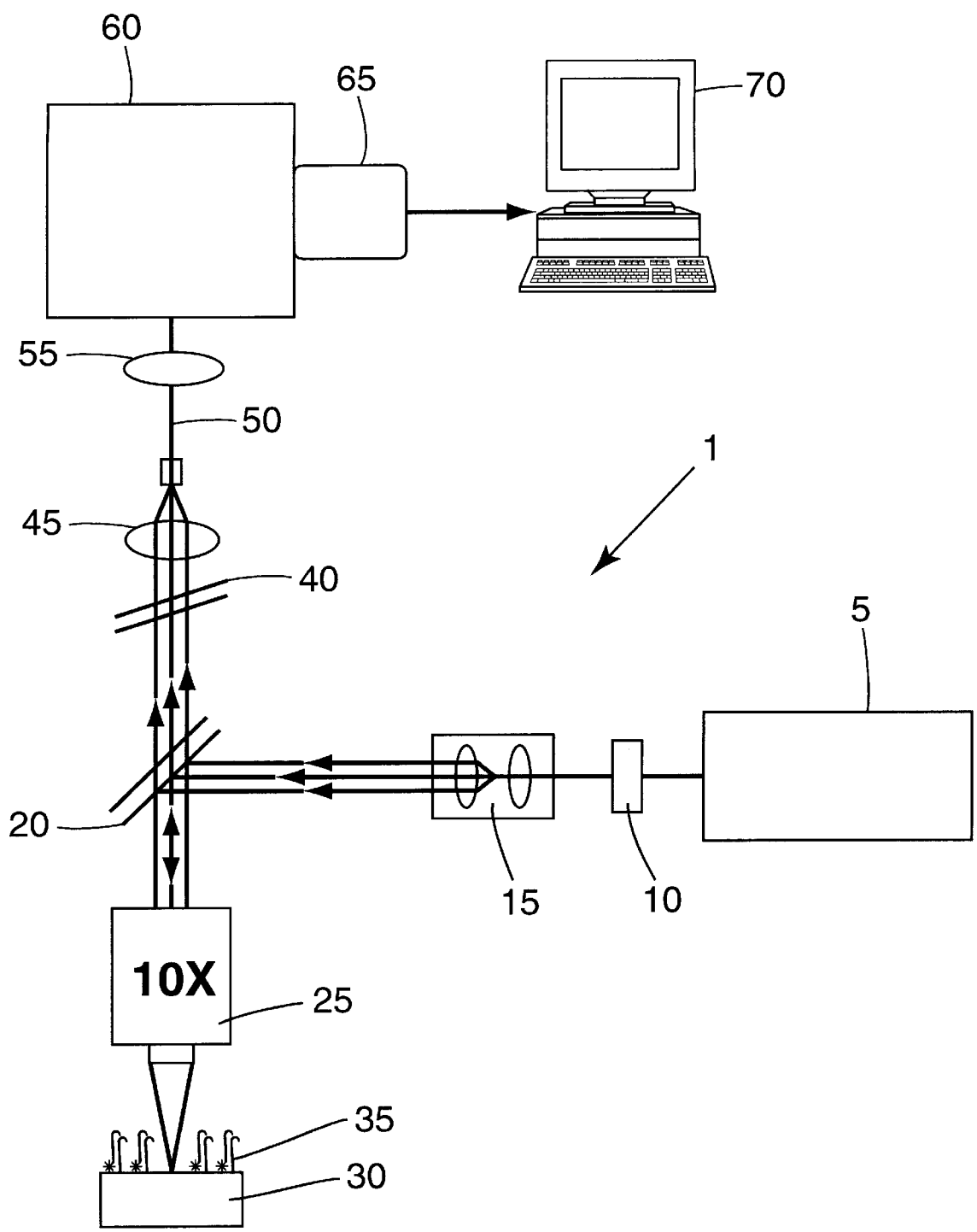
FIG. 17 is a schematic diagram of a SER gene probe detection system.

FIG. 17 is a schematic diagram of a SER gene probe detection system 1. The system comprises an energy source 5, a bandpass filter 10, a beam expander 15, a holographic beam splitter 20, a 10× objective lens 25, a SER-activated substrate 30, the SER-activated substrate 30 having hybridized SER gene probes 35, a Raman holographic notch filter 40, coupling optics 45, an optical fiber 50, optics 55, a polychromator detector 60 being a signal analyzer equipped with a charge-coupled device (CCD) 65 and a data processor 70. The signal analyzer 60 equipped with the CCD 65 and the data processor 70 provide an analyzing means for detecting and identifying hybridized target oligonucleotide strands.

An example of Instrumentation components for the experimentation were as follows. Laser excitation was the 647.1-nm emission line of a krypton laser (Coherent, Innova 70), which was spectrally purified with a 10-cm-$^1$ bandwidth bandpass filter (Corion). Other lasers available for excitation into the UV absorption band of the SER label include the nitrogen laser, (Laser Science Inc.) at 337 nm, and the helium-cadmium laser, (Liconox) at 325 nm, for use in the production of surface-enhanced resonance Raman scattering (SERRS) signal. In order to achieve a tight focus and highly efficient SERS signal collection, the laser beam was expanded and collimated before being focused onto the sample with a 6× objective lens (Newport, Model L6X). Furthermore, the objective lens was used to both excite the sample and collect the SERS signal. This end-on excitation/collection geometry was made possible by using a holographic beam splitter (Kaiser Optical Systems, Inc., Model HB 647–26N18). As the expanded excitation laser beam was deflected 90° C. and properly focused onto the sample, the corresponding SERS signal beam was collected, collimated, and projected through the beam splitter, thus isolating the SERS signal beam from the incident laser beam. A holographic notch filter (Kaiser Optical Systems, Inc., HNPF-647–1.0) was placed in the SERS signal beam to further reject Rayleigh scattered radiation. The expanded signal beam was finally focused onto a 600-$\mu$m core optical fiber (Fiberguide Industries), which transmitted the signal to the spectrometer. The intensity was monitored at the point of sample excitation and maintained at 25 mW for all measurements.

Tuning of a birefringent filter plus the use of a bandpass filter permitted a narrow excitation bandpass centered at 620 nm. Laser power was 25 mW for all measurements. A right-angle geometry of the laser excitation source and the scattered radiation was employed. SERS measurements were performed using two experimental systems. The SPEX-based system was used to generate the basic SERS spectra. Raman and SERS measurements were conducted with a SPEX Model 1403 double-grating spectrometer (SPEX Inc.) with 2 cm-, bandpass. Signal detection was performed using a thermoelectrically cooled gallium arsenide photomultiplier tube (Burle Industries Model C3103402), operated in the photon counting mode. Data storage and processing were handled using a personal computer (PC) with SPEX DM-3000 software. Alternatively, an ICCD-based system was used to generate spectra in hybridized experiments. In this system, the 632.8-nm line from a helium-neon laser was used with an excitation power of approximately 5 mW. A bandpass filter was used to spectrally isolate the 632.8-nm line before focusing onto the sample. Scattered radiation was collected with a two-lens system which efficiently coupled the collected radiation to a 600 $\mu$m diameter silica fiber (NA-0.26, General Fiber Optics). Signal collection was performed at 180° with respect to the incident laser beam. A Raman holographic filter was used to reject the Rayleigh scattered radiation prior to entering the collection fiber. The collection fiber was finally coupled to a spectrograph (ISA, HR-320) which was equipped with a red-enhanced intensified charge-coupled device (RE-ICCD) detection system (Princeton Instruments, RE-ICCD-576S). ICCD control and data processing was enabled by a Princeton Instruments ST-130 control unit and CSMA software installed on a PC. Other 2-dimensional detectors can also be used such as charged injection device (CID) or photodiode arrays or phototransistor arrays.

All buffers and reagents were molecular biology grade (DNAse and RNAse free) and were sterilized by autoclaving. Only sterilized plastic ware (microcentrifuge tubes, pipette tips etc.,) were used for all procedures. All DNA manipulations were performed as described by Sambrook et al (*Molecular Cloning. A Laboratory Manual*, Second edition, Cold Spring Harbor Laboratory Press), incorporated herein by reference. All solutions were prepared with distilled, deionized Milli-Q Plus water. All nucleic acid solutions were sterilized by autoclaving or by filtration through a 0.22-$\mu$m filter. Exposure of labeled DNA to light was minimized by using opaque siliconized glassware, aluminum foil covering, or reduced room-lighting conditions.

Mutation of one gene, BRCA1 is believed to account for approximately 45% of families with significantly high breast cancer incidence and at least 80% of families with increased incidence of both early-onset breast cancer and ovarian cancer. A candidate gene mutation, which influences susceptibility to breast and ovarian cancer has been identified by positional cloning methods (Miki Y. et al, *Science*, 266 (1994), 66). The mutation includes an 11-base pair deletion, a 1-base pair insertion, a stop codon, a missense substitution, and an inferred regulation deletion.

EXAMPLE 1

Preparation of Buffers and Reagents

Synthetic DNA templates are developed specifically for diagnosis of various disease and detection of varial bacterial systems. For cancer diagnostics, the synthetic DNA templates from a specific region of the BRCA1 gene that exhibits 11-base pair deletion are utilized as a model system to test the utility of the PHA SERGene probe system for BRCA1 detection. The method involves using a cresyl fast violet (CFV)-labeled DNA sequence as a primer in PCR amplification of the target DNA and hybridization to a capture probe sequence which is an internal sequence of the amplified product covalently bound onto a polystyrene substrate. All the oligonucleotides used in the example are purchased or synthesized using an Expedite 8909 nucleic acid synthesizer (Millipore). Expedite reagents are used providing faster synthesis, and deprotection times. The oligonucleotides are cleaved from the column by incubating the controlled pore glass (CPG) in ammonium hydroxide at room temperature for 2 hours. The dimethyl trityl protection groups on the nucleotides are removed by incubation with ammonium hydroxide at 55° C. for 30 minutes. Ammonium hydroxide is removed by vacuum evaporation and the oligonucleotides are resuspended in sterile distilled water at a concentration of 10 $\mu$g/$\mu$l.

Binding of the Capture Probe and Labeling

Capture probe sequences synthesized with a 5' amino linker are purified as described above and resuspended in 0.1-M carbonate buffer (pH 9.0) at a final concentration of 1 $\mu$g/$\mu$l and are spotted onto a nylon membrane and incubated at 37° C. for one hour. (In another experiment, N-oxysuccinimide (NOS)-derivatized polystyrene plates (DNA-BIND from Corning-Costar) are used as the substrate). Unbound DNA is removed by washing several times in phosphate buffered saline.

Cresyl fast violet-labelled oligonucleotide primers are prepared using a modification of the procedure described by Chu and Orgel (*Nucleic Acids Res,* 1983, 11, p. 6513), incorporated herein by reference; also described by Vo-Dinh et al (*Analytical Chemisty*, 1994, 33, pp. 3379–3383), incorporated herein by reference. Approximately 10 micrograms of the oligonucleotides are dried down by vacuum evaporation in a microcentrifuge tube and 50 $\mu$l of 0.2 M imidazole (1,3-Diaza-2,4-cyclopentadiene) at pH 8.0, and 50 $\mu$l of 50 mM 1-ethyl-3-(dimethylamino)propyl carbodiimide (EDC)

in 2-(N-Morpholino)ethanesulfonic acid (MES) buffer at pH 8.0 is added and incubated at 50° C. for 3 hours. This treatment results in the conversion of phophoramidites to 5' phosphorimidazolides. One hundred microliters of a saturated solution of CFV in sterile distilled water are added and incubated for 18 hours at 50° C. The unreacted CFV is removed by gel filtration using a Sephadex GIO (Pharmacia) column equilibrated with 0.1 M borate buffer pH 8.0. The void volume containing the CFV-labeled DNA is collected and concentrated by vacuum evaporation. This product is resuspended in distilled water and further purified by isopropanol precipitation, and washed in 50% isopropanol several times to remove any traces of unbound CFV.

Polymerase Chain Reaction Procedure

Polymerase Chain reaction (PCR) amplification of target template DNA is performed in 50 μl aliquots using a Coy thermal cycler as follows: The amplification reactions are performed in 100 mM Tris-HCl, (pH 8.3) containing 50 mM KCl, 1.5 mM $MgCl_2$, 0.01% gelatin with 10 nanograms of purified template DNA, 20 μM of each of the two primers, and 3 μM of each of the four deoxynucleoside triphosphates (dATP, DCTP, dGTP and dTIP). Amplifications are performed with initial heating at 95° C. for 5 minutes to denature the template followed by denaturation for 30 seconds at 94° C., annealing for 30 seconds at 50° C., and extension for 30 seconds at 72° C. for 30 cycles. Ten microliters of the reaction are electrophoresed on 1% Agarose gels in Tris Borate buffer (44.5 mM Tris, 4-.5 mM borate pH 8.3) to detect the amplified product. After PCR with CFV labelled primer, 15 μl of the amplification mixture are removed for electrophoretic detection of the product and 15 μL 20× SSC (0.3 M sodium citrate, pH 7.0 containing 3.0 M sodium chloride) are added. This process results in bringing the amplified target DNA to a final concentration of 5× SSC suitable for hybridization. This solution is heated to boiling to dissociate double-stranded DNA and is used directly for hybridizations. Note, the PCR procedure is optional. If the detection sensitivity is sufficient, PCR is not required, and the detection can be performed right after hybridization.

Hybridization Procedure

An important step in gene probe analysis involve hybridization. The unreacted sites on the nylon membrane are blocked by adding 200 μl of 3% Bovine Serum Albumin (BSA) in 0.1-M carbonate buffer (pH 9.0) and incubating at 37° C. for 30 minutes. One hundred microliters of probe DNA at a concentration of 100 ng/ml in hybridization solution (5× SSC containing 1.0% Carnation non fat dry milk, 0.02% Sodium dodecyl sulfate) is added to each well and hybridizations are performed at 5° C. below the $T_m$ (melting temperature of the capture probe sequence) for one hour. The double-stranded PCR amplifier probe sequence is denatured by boiling in water for 5 minutes and rapidly chilling on ice to prevent DNA strand reassociation. The resulting PCR reaction mixture is directly used as the probe.

SERS Detection System a) A Raman spectrometer or detection system is used to detect the SERS gene probe, as illustrated in FIG. 17. Raman and SERS spectrum measurements are recorded using a SPEX 1403 double grating spectrometer with 2 $cm^{-1}$ bandpass. Signal detection is performed using a thermoelectrically cooled gallium arsenide photomultiplier tube (Burle Industries Model C3103402) operated in the photon counting mode. Data acquisition and processing is enabled with the SPEX DM-3000 software. The excitation source is the 647.1-nm emission line of a krypton laser (Coherent, Innova 70), which is spectrally purified with a 10-$cm^{-1}$ bandwidth bandpass filter (Corion). In order to achieve a tight focus and highly efficient SERS signal collection, the laser beam is expanded and collimated before being focused onto the sample with a 6× objective lens (Newport, Model L6X). Furthermore, the objective lens is used to both excite the sample and collect the SERS signal. This end-on excitation/collection geometry is made possible by using a holographic beam splitter (Kaiser Optical Systems, Inc., Model HB 647-26N18). As the expanded excitation laser beam is deflected 90° and properly focused onto the sample, the corresponding SERS signal beam is collected, collimated, and projected through the beam splitter, thus isolating the SERS signal beam from the incident laser beam. A holographic notch filter (Kaiser Optical Systems, Inc. HNPF-647–1.0) is placed in the SERS signal beam to further reject Rayleigh scattered radiation. The expanded signal beam is finally focused onto a 600-μm core optical fiber (Fiberguide Industries), which transmits the signal to the spectrometer. The intensity is monitored at the point of sample excitation and maintained at 25 mW for all measurements. Another detection system that can be used includes a charge-coupled device (CCD) equipped with a polychromator to record Raman and SERS spectrum. FIG. 17 shows the schematic diagram of the instrumental set-up using a polychromator equipped with a CCD.

Experiments can also be conducted and measurements taken using the procedures given in Example 1 in which PCR is not performed and SERS of DNA labeled with CFV is detected.

In the example, unlabelled DNA molecules are covalently linked onto the substrate and then hybridized with the complementary DNA sequence labelled with CFV, and the hybridizations are detected by the SERS signals from CFV. The capture probe sequences are bound on to the substrate and the PCR amplification products BRCA1. PCR reaction performed with the BRCA1 synthetic template as target and the primers are diluted with 20× SSC (as discussed above in Example 1 and are used directly as the hybridization mixture on the capture probe bound surfaces. After hybridization, the substrates are SER-activated by coating them with silver (nanospheres) using thermal evaporation, and the SERS spectra are recorded. Other means of SER activation of the support means can also be used, such as, either dipping the support means into a colloidal solution of metal nanoparticle hydrosols, or by delivering the metal nanoparticles in the colloidal solution of metal nanoparticle hydrosol to the surface of the support means.

Another gene probe is used to detect a mutation at codon 717 of the beta-amyloid precursor protein gene which has been found to cosegregate with familial Alzheimer's disease (MC Chartier-Harlin et al, *Nature,* 353 (1991), 844846). Direct sequencing of exon 17 in affected individuals from this family has revealed a base change producing a Val-Gly substitution at codon 717. Synthetic DNA templates using this mutation can also be developed and utilized in the procedure described in EXAMPLE 1.

Another example of using a gene probe is used to detect a human glucokinase gene mutation (based on two missense mutations) which was linked to early onset non-insulin—dependent (type 2) diabetes mellitus (M. Stoffel et al, *Proc. Natl. Acad. Sci. U.S.A.,* 89 (16)(1992), 7698–7702). Synthetic DNA templates using this mutation can also be developed and utilized in the procedure described in EXAMPLE 1.

Another example of using a gene probe to detect neoplastic transformation in the normal brain which may occur as a result of the accumulation of a series of genetic alterations. These genetic alterations include the loss, gain or amplification of different chromosomes which lead to altered expression of proteins that play important roles in the regulation of cell proliferation. These alterations lead to changes in the expression of several genes. Recent studies suggest that altered expression of several genes: p53 (protein 53), RB (retinoblastoma), INF (interferon), VEGF (vascular endothelial growth factor), TGF beta (transforming growth factor beta), CD44, etc. The procedure of EXAMPLE 1 can also be used for these genes as well.

EXAMPLE 2

Synthetic DNA templates from the gag region of HIV1 were utilized as a model system to test the utility of the PHA SERGene probe system for HIV1 detection. The method involved using a cresyl fast violet (CFV)-labeled DNA sequence as a primer in PCR amplification of the target DNA and hybridization to a capture probe sequence which is an internal sequence of the amplified product covalently bound onto a polystyrene substrate. All the oligonucleotides used in the example were synthesized using an Expedite 8909 nucleic acid synthesizer (Millipore). Expedite reagents were used providing faster synthesis, and deprotection times. The oligonucleotides were cleaved from the column by incubating the controlled pore glass (CPG) in ammonium hydroxide at room temperature for 2 hours. The dimethyl trityl protection groups on the nucleotides were removed by incubation with ammonium hydroxide at 55° C. for 30 minutes. Ammonium hydroxide was removed by vacuum evaporation and the oligonucleotides were resuspended in sterile distilled water at a concentration of 10 $\mu g/\mu l$.

Binding of the Capture Probe and Labeling

Capture probe sequences synthesized with a 5' amino linker were purified as described above and resuspended in 0.1-M carbonate buffer (pH 9.0) at a final concentration of 1$\mu g/\mu l$ and was spotted onto a nylon membrane. (In another experiment, N-oxysuccinimide (NOS)-derivatized polystyrene plates (DNA-BIND from Corning-Costar) were used as the substrate) and incubated at 37° C. for one hour. Unbound DNA was removed by washing several times in phosphate buffered saline.

Cresyl fast violet-labelled oligonucleotide primers were prepared using a modification of the procedure described by Chu and Orgel (*Nucleic Acids Res,* 1983, 11, p. 6513), incorporated herein by reference; also described by Vo-Dinh et al (*Analytical Chemisty,* 1994, 33, pp. 3379–3383), incorporated herein by reference. Approximately 10 micrograms of the oligonucleotides were dried down by vacuum evaporation in a microcentrifuge tube and 50 $\mu l$ of 0.2 M imidazole (1,3-Diaza-2,4-cyclopentadiene) at pH 8.0, and 50 $\mu l$ of 50 mM 1-ethyl-3-(dimethylamino)propyl carbodiimide (EDC) in 2-(N-Morpholino)ethanesulfonic acid (MES) buffer at pH 8.0 was added and incubated at 50° C. for 3 hours. This treatment resulted in the conversion of phophoramidites to 5' phosphorimidazolides One hundred microliters of a saturated solution of CFV in sterile distilled water was added and incubated for 18 hours at 50° C. The unreacted CFV was removed by gel filtration using a Sephadex G10 (Pharmacia) column equilibrated with 0.1 M borate buffer pH 8.0. The void volume containing the CFV-labeled DNA was collected and concentrated by vacuum evaporation. This product was resuspended in distilled water and further purified by isopropanol Ace precipitation, and washed in 50% isopropanol several times to remove any traces of unbound CFV.

Polymerase Chain Reaction Procedure

Polymerase Chain reaction (PCR) amplification of target template DNA was performed in 50 $\mu l$ aliquots using a Coy thermal cycler as follows: The amplification reactions were performed in 100 mM Tris-HCl, (pH 8.3) containing 50 mM KCl, 1.5 mM $MgCl_6$; 0.01% gelatin with 10 nanograms of purified template DNA, 20 $\mu M$ of each of the two primers, and 3 $\mu M$ of each of the four deoxynucleoside triphosphates (dATP, dCTP, dGT and dTTP). Amplifications were performed with initial beating at 95° C. for 5 minutes to denature the template followed by denaturation for 30 seconds at 94° C., annealing for 30 seconds at 50° C., and extension for 30 seconds at 72° C. for 30 cycles. Ten microliters of the reaction was electrophoresed on 1% Agarose gels in Tris Borate buffer (44.5 mM Tris, 4-.5 mM borate pH 8.3) to detect the amplified product. After PCR with CFV labelled primer, 15 $\mu l$ of the amplification mixture were removed for electrophoretic detection of the product and 15 $\mu l$ 20× SSC (0.3 M sodium citrate, pH 7.0 containing 3.0 M sodium chloride) were added. This process resulted in bringing the amplified target DNA to a final concentration of 5× SSC suitable for hybridization. This solution was heated to boiling to dissociate double-stranded DNA and was used directly for hybridizations. Note, the PCR procedure is optional. If the detection sensitivity is sufficient, PCR is not required, and the detection can be performed right after hybridization.

Hybridization Procedure

An important step in gene probe analysis involve hybridization. The unreacted sites on the nylon membrane were blocked by adding 200 $\mu l$ of 3% Bovine Serum Albumin (BSA) in 0.1-M carbonate buffer (pH 9.0) and incubating at 37° C. for 30 minutes. One hundred microliters of probe DNA at a concentration of 100 ng/ml in hybridization solution (5× SSC containing 1.0% Carnation non fat dry milk, 0.02% Sodium dodecyl sulfate) was added to each well and hybridizations were performed at 5° C. below the $T_m$ (melting temperature of the capture probe sequence) for one hour. The double-stranded PCR amplifier probe sequence was denatured by boiling in water for 5 minutes and rapidly chilling on ice to prevent DNA strand reassociation. The resulting PCR reaction mixture was directly used as the probe.

SERS Detection System a) A Raman spectrometer or detection system was used to detect the SERS gene probe, as illustrated in FIG. 17. Raman and SERS spectrum measurements are recorded using a SPEX 1403 double grating spectrometer with 2 $cm^{-1}$ bandpass. Signal detection was performed using a thermoelectrically cooled gallium arsenide photomultiplier tube (Burle Industries Model C3103402) operated in the photon counting mode. Data acquisition and processing was enabled with the SPEX DM-3000 software. The excitation source was the 647.1-nm emission line of a krypton laser (Coherent, Innova 70), which was spectrally purified with a 10-$cm^{-1}$ bandwidth bandpass filter (Corion). In order to achieve a tight focus and highly efficient SERS signal collection, the laser beam was expanded and collimated before being focused onto the sample with a 6× objective lens (Newport, Model L6X). Furthermore, the objective lens was used to both excite the sample and collect the SERS signal. This end-on excitation/collection geometry was made possible by using a holographic beam splitter (Kaiser Optical Systems, Inc., Model HB 647–26N18). As the expanded excitation laser beam was deflected 90° and properly focused onto the sample, the corresponding SERS signal beam was collected, collimated, and projected through the beam splitter, thus isolating the SERS signal beam from the incident laser beam. A holographic notch filter (Kaiser Optical Systems, Inc. HNPF-647-1.0) was placed in the SERS signal beam to further reject Rayleigh scattered radiation. The expanded signal beam was finally focused onto a 600-$\mu$m core optical fiber (Fiberguide Industries), which transmitted the signal to the spectrometer. The intensity was monitored at the point of sample excitation and maintained at 25 mW for all measurements. Another detection system used includes a CCD equipped with a polychromator to record Raman and SERS spectrum. FIG. 17 shows the schematic diagram of the instrumental set-up using a polychromator equipped with a charge-coupled device.

Experiments were also conducted and measurements taken using the procedures given in Example 2 in which PCR was not performed and SERS of DNA labeled with CFV was detected.

In the example, unlabelled DNA molecules were covalently linked onto the substrate and then hybridized with the complementary DNA sequence labelled with CFV, and the hybridizations were detected by the SERS signals from CFV. The capture probe sequences were bound on to the substrate and the PCR amplification products HIV1 PCR reaction performed with the HIV1 synthetic template as target and the primers were diluted with 20x SSC (as discussed above in Example 2 and was used directly as the hybridization mixture on the capture probe bound surfaces. After hybridization, the substrates were SER activated by coating them with silver (nanospheres) using thermal evaporation, and the SERS spectra were recorded. Other methods of SER activating the support means can also be used, such as, either dipping the support means into a colloidal solution of metal nanoparticle hydrosols, or by delivering the metal nanoparticles in the colloidal solution of metal nanoparticle hydrosol to the surface of the support means. The results obtained with the HIV1 hybridization experiments, shows the SERS detection of the double-stranded DNA after PCR. No CFV signals were observed when hybridizations were performed with a capture probe sequence which was not complementary to the HIV1 template used. No non-specific binding of CFV to the nylon substrate was detected. These results demonstrated the effectiveness of Applicant's SERGene probe technique.

Figure 18:
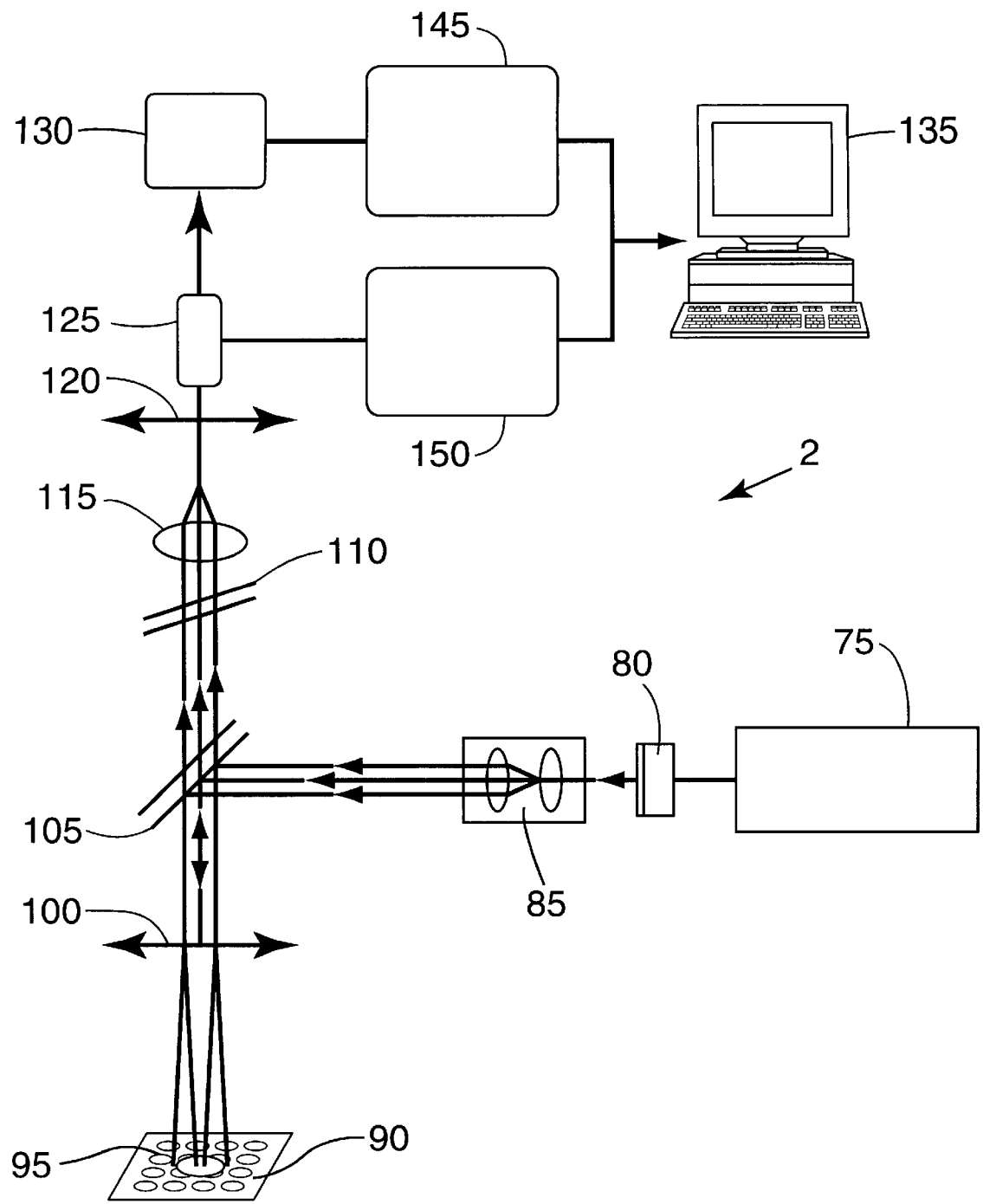
FIG. 18 is a schematic diagram of an integrated system for SER-based DNA mapping and sequencing using 2-dimensional spectral imaging.

FIG. 18 shows a schematic of an integrated system for SERS-Based DNA mapping and sequencing using 2-dimensional spectral imaging. This system is used for DNA sequencing and mapping applications. FIG. 18 shows the integrated imaging system 2 using an acousto-optic tunable filter (AOTF) 125 for spectral imaging of SER gene probes. AOTFs are a relatively new technology used to isolate one or more wavelengths of light. They operate as a tunable optical band pass filter. In contrast, to a grating monochromator, an AOTF offers the advantage of having no moving parts and can be scanned at very high rates (millisecond time scale) without the possibility of error due to gear backlash or other mechanical problems. Since AOTFs with high spatial resolution (typically 100 lines per mm) and large optical apertures are available, they can be applied for spectral imaging applications. An alternative to AOTF, a filter system that can be used, includes the liquid crystal tunable filter (LCTF).

FIG. 18 represents the integrated imaging system 2 comprising a laser excitation source 75, a bandpass filter 80, a beam expander 85, a holographic beam splitter 105, imaging optics 100, a SERS activated support means 90, the SER activated support means 90 having hybridized SER gene probes 95 on the surface of the SER activated support means, a Raman holographic notch filter 110 optics 115, imaging optics 120, an AOTF 125, a charge coupled device camera 130, a CCD driver 145, an AOTF driver 150 and a data processor 135 provide an analyzing means for detecting and identifying hybridized target oligonucleotide strands.

The SERS light emitted from the sample was collected by an imaging lens 100, filtered by the AOTF, and then imaged onto a CCD. By changing the wavelength of the AOTF, a spectrum could be acquired as a series of images (one for each wavelength). The $TeO_2$ AOTF used in this work was purchased from Brimrose, Baltimore, Md. (model TEAF 10-45-70-S).

The radio-frequency (rf) generator used (Brimrose-model AT) could apply 0 to 25 W of rf power and was controlled by a DOS-based computer using a 16-bit computer controller board supplied by Brimrose. A custom software was developed at Oak Ridge National Laboratory to control the AOTF, supporting various scanning modes and fixed-frequency operation.

The CCD is a model ST-6 purchased from Santa Barbara Instrument Group, Santa Barbara, Calif., based on a Texas Instruments TC241 CCD detector. The operating spectral range is 330 to 1100 nm. The detector is 8.63×6.53 mm and has a resolution of 750×242 pixels, with a two pixels horizontal binning giving an effective resolution of 375×242 pixels. Standard pixel size is 23×27 $\mu$m. Dark current can be kept as low as 13 electron/pixel/second at −20° C. The detector is installed on a regulated thermoelectric Peltier effect based cooler. Anti-blooming protection is also included. The analog-to-digital resolution is 16 bits. A mechanical shutter is included in the optical head to facilitate taking dark frames. The CCD controller is based on the IBM 8088 microprocessor and runs at 8 kHz. The interface to the PC compatible computer is accomplished through a regular RS232 cable and baud rate is 115.2 baud. Other 2-dimensional detectors can be used such as charged injection devices (CID) or photodiode arrays or phototransistor arrays.

Figure 19:
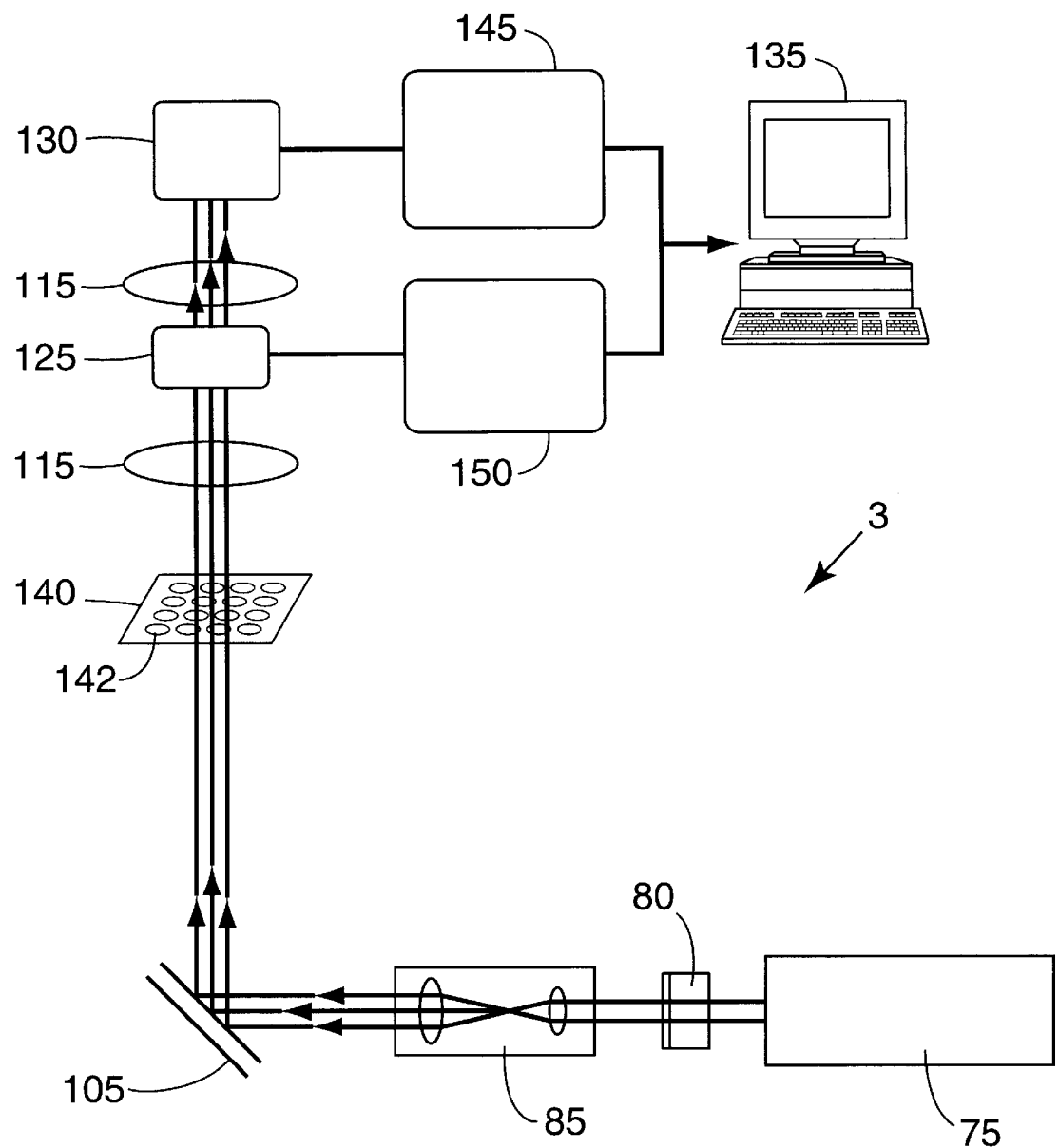
FIG. 19 is a schematic diagram of a detection system for spectral imaging of the SER-labeled gene probes in a hybridization array format.

FIG. 19 shows a schematic diagram of a typical detection system for spectral imaging of the SER gene probes in a hybridization array format. The system 3 uses a charge-coupled device 145. Such a system allows simultaneous 2-dimensional detection of multiple hybridization spots 142 directly on the support means (substrate) 140 at selected wavelength (e.g., main SERS peaks of the different labeled probes). A helium neon (632.8 nm) or a krypton (647.1 nm) laser 75 can be used as the excitation source for this system. The laser beam will be spectrally purified with an appropriate bandpass filter 80, then expanded with a beam expander 85 and collimated at the appropriate beam diameter for full field irradiation and directed onto one side of the SER support means (substrate) 140, e.g., the back side of the support means with no active coating using a mirror 105.

Alternatively, front-side excitation geometry, as in FIG. 18, is also possible by using a beam splitter to separate the laser excitation path and the detection path. An appropriate holographic Raman notch filter may be used to reject the laser scatter light. Imaging optics 115 of a conventional optical microscope is used to collect the signal and produce the SERS-based image of the hybridization spot array on the imaging ICCD. In FIG. 19, the system utilizes an AOTF 125 for spectral imaging of SER gene probes, optics 115, a CCD camera 144, a CCD driver 145, an AOTF driver 150, and a data processor 135.

Figure 20:
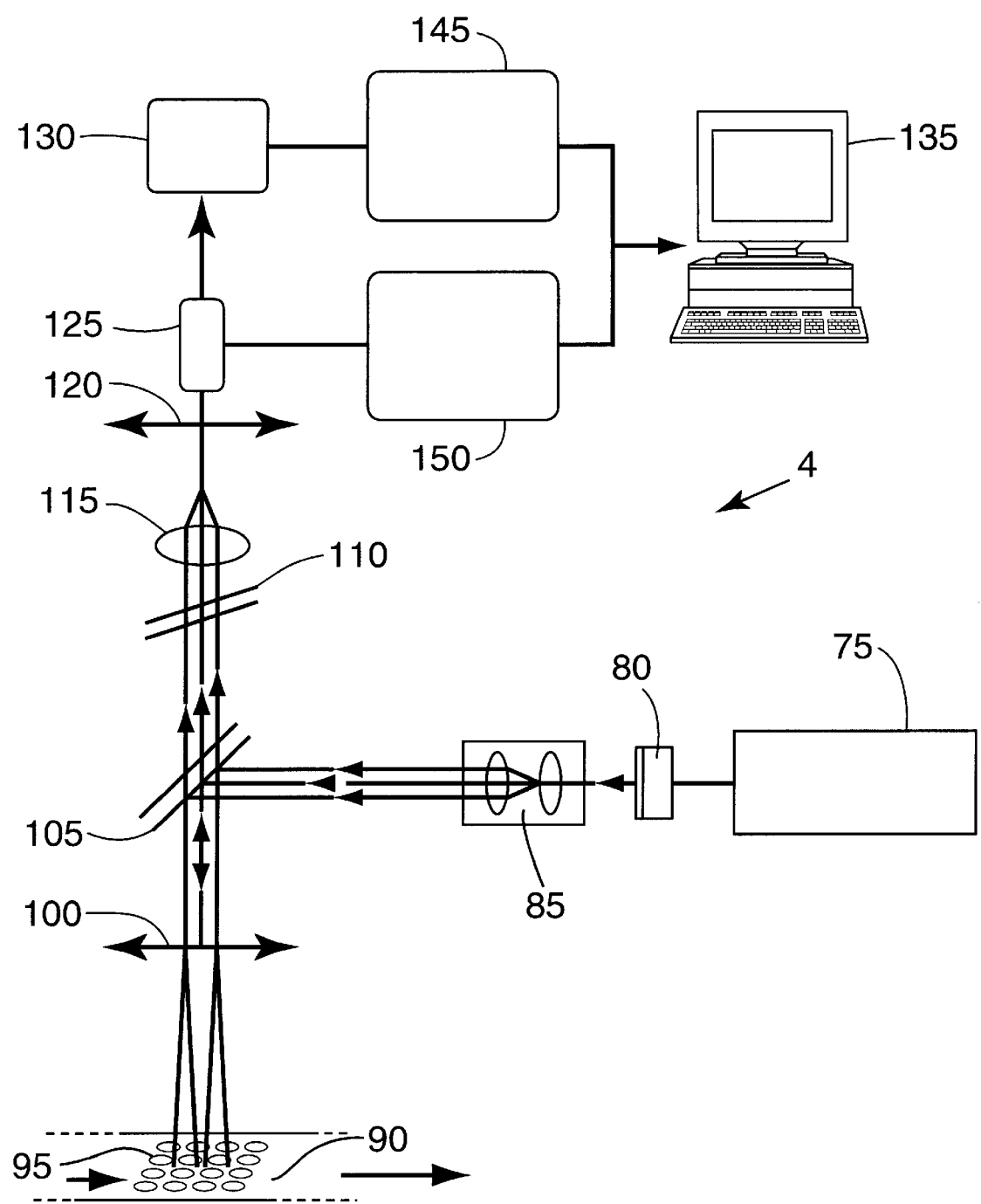
FIG. 20 is a schematic diagram of an integrated imaging system for spectral imaging of the SER gene probes that are absorbed on a continuous-moving support means.

FIG. 20 shows a schematic of an integrated imaging system for spectral imaging of the SER gene probes that are adsorbed on a continuous-moving support means. This system is used for DNA sequencing and mapping applications. FIG. 20 shows the integrated imaging system 4 using an acousto-optic tunable filter (AOTF) 125 for spectral imaging of SER gene probes 95. An alternative to AOTF, a filter system that can be used, includes the liquid crystal tunable filter (LCTF).

FIG. 20 represents the integrated imaging system 4 comprising a laser excitation source 75, a bandpass filter 80, a beam expander 85, a holographic beam splitter 105, imaging optics 100, a continuous-moving SER activated support means 90, the SER activated support means 90 having hybridized SER gene probes 95 on the surface of the SER activated support means, a Raman holographic notch filter 110, optics 115, imaging optics 120, an AOTF 125, a charge coupled device camera 130, a CCD driver 145, an AOTF driver 150 and a data processor 135 provide an analyzing means for detecting and identifying hybridized target oligonucleotide strands. Examples of the continuous-moving SER activated support means 90 includes a moving tape or a rotating disk. The continuous-moving support means system is useful in continuous high-throughput chemical, biological, pharmaceutical assays, such as drug screening and drug discovery analysis.

The SERS light emitted from the sample was collected by an imaging lens 100, filtered by the AOTF, and then imaged onto a CCD. By changing the wavelength of the AOTF, a spectrum could be acquired as a series of images (one for each wavelength). The $TeO_2$ AOTF used in this work was purchased from Brimrose, Baltimore, Md. (model TEAF 10-45-70-S).

The radio-frequency (rf) generator used (Brimrose-model AT) could apply 0 to 25 W of rf power and was controlled by a DOS-based computer using a 16-bit computer controller board supplied by Brimrose. A custom software was developed at Oak Ridge National Laboratory to control the AOTF, supporting various scanning modes and fixed-frequency operation.

The CCD is a model ST6 purchased from Santa Barbara Instrument Group, Santa Barbara, Calif., based on a Texas Instruments TC241 CCD detector. The operating spectral range is 330 to 1100 nm. The detector is 8.63×6.53 mm and has a resolution of 750×242 pixels, with a two pixels horizontal binning giving an effective resolution of 375×242 pixels. Standard pixel size is 23×27 μm. Dark current can be kept as low as 13 electron/pixel/second at −20° C. The detector is installed on a regulated thermoelectric Peltier effect based cooler. Anti-blooming protection is also included. The analog-to-digital resolution is 16 bits. A mechanical shutter is included in the optical head to facilitate taking dark frames. The CCD controller is based on the IBM 8088 microprocessor and runs at 8 kHz. The interface to the PC compatible computer is accomplished through a regular RS232 cable and baud rate is 115.2 baud. Other 2-dimensional detectors can be used such as charged injection devices (CID) or photodiode arrays or phototransistor arrays.

There has been shown and described what are at present considered the preferred embodiments of the invention, it will be obvious to those skilled in the art that various changes and modifications can be made therein, without departing from the scope of the invention defined by the appended claims.

What is claimed is:

1. A method for using a Surface-Enhanced Raman (SER)-labeled Gene Probe for hybridization, detection and identification of SER-labeled hybridized target oligonucleotide material comprising the steps of:
    a) providing a support means;
    b) preparing a solution of gene probe oligonucleotide strands of known sequence, said oligonucleotide strands being complementary to a target oligonucleotide strand;
    c) disposing said gene probe oligonucleotide strands onto said support means;
    d) incubating said support means having said disposed gene probe oligonucleotide strands for a period of time sufficient enough to immobilize said oligonucleotide strands on said support means;
    e) synthesizing at least one SER-labeled oligonucleotide strand of unknown sequence taken from a target sample being suspect of containing target oligonucleotide strands, said SER-labeled oligonucleotide strand having at least one SER label;
    f) preparing a SER-labeled oligonucleotide solution comprising at least one SER-labeled oligonucleotide strand wherein said SER label is unique for said target oligonucleotide strand of a particular sequence;
    g) incubating said support means having said immobilized gene probe oligonucleotide strands thereon in an amount of said SER-labeled oligonucleotide solution sufficient enough to provide an amount of said SER-labeled target oligonucleotide strands that are complementary to said immobilized gene probe oligonucleotide strands to contact said immobilized gene probe oligonucleotide strands, incubating for a time period sufficient as for said SER-labeled target oligonucleotide strands to contact said immobilized gene probe oligonucleotide strands and sufficient enough as for hybridization to occur, thereby producing SER-labeled hybridized target oligonucleotide material;
    h) removing said SER-labeled oligonucleotide strands that did not hybridize to said immobilized gene probe oligonucleotide strands;
    i) activating said support means with a SER activating means, said support means having SER-labeled hybridized target oligonucleotide material; and
    j) analyzing said SER-activated support means having SER-labeled hybridized target oligonucleotide material.

2. The method of claim 1 wherein said oligonucleotide strands comprise strands of Deoxyribonucleic acid, Ribonucleic acid or peptide nucleic acid.

3. The method of claim 1 wherein said support means is a substrate suitable for hybridization.

4. The method of claim 1 wherein said support means is a membrane suitable for hybridization.

5. The method of claim 1 wherein said support means is a blotting material.

6. The method of claim 1 wherein said support means is a polymer-based nanosphere.

7. The method of claim 1 wherein said support means is an alumina-based nanoparticle.

8. The method of claim 1 wherein said support means is a titanium oxide nanoparticle.

9. The method of claim 1 wherein said support means has a surface comprising cellulose, silica gel or polystyrene.

10. The method of claim 1 wherein said SER activating means comprises the step of coating said support means with metal-coated magnetic nanobeads.

11. The method of claim 1 wherein said SER activating means comprises inducing an electrochemical reaction to roughen the surface of said support means on which said hybridization occurs.

12. The method of claim 1 wherein said SER activating means comprises blotting said SER-labeled hybridized target oligonucleotide material directly onto a SER active support means using a blotting technique.

13. The method of claim 12, wherein said blotting technique comprises applying an electric field to adsorb said SER-labeled hybridized target oligonucleotide material onto a SERS active blot.

14. The method of claim 1 wherein said support means is disposed on a fiberoptic probe having a probe tip which supports said SER-activated support means, said fiberoptic probe having at least one optical fiber for transmitting exciting optical energy from an energy source to said SER-labeled gene probe on said SER-activated support means on said fiberoptic probe tip to generate a Raman optical signal and for collecting and transmitting said Raman optical signal to a signal analyzer.

15. The method of claim 1 wherein multiple SER-activated support means are disposed on an array of optical fibers for performing multiple assays, each said optical fiber having a fiberoptic tip which supports said SER-activated support means, said support means having uniquely labeled SER-labeled hybridized target oligonucleotide material wherein said SERS label is unique for a target oligonucleotide complementary to said gene probe oligonucleotide, said array further having an energy source for generating exciting optical energy and means for directing said exciting optical energy onto said optical fibers, and said optical fibers transmitting said exciting optical energy to said SER gene probe on said SER-activated support means on said fiberoptic probe tip to generate a Raman optical signal, said array further having means for collecting and transmitting said Raman optical signal to an array of signal analyzers.

16. The method of claim 1 wherein said SER-activated support means is disposed on a waveguide having a surface which supports said SER-activated support means, said waveguide further having means for transmitting exciting optical energy from an energy source to said surface and to said SER-labeled gene probe to generate a Raman optical signal and means for collecting and transmitting said Raman optical signal to a signal analyzer.

17. The method of claim 1 wherein, multiple SER-activated support means are disposed on a waveguide having a surface which supports said multiple SER-activated support means, each of said SER-activated support means having SER-labeled gene probes labeled uniquely for a particular target oligonucleotide complementary to said gene probe oligonucleotide strand, said waveguide further having means for transmitting exciting optical energy from an energy source to said surface and to said SER-labeled gene probe to generate a Raman optical signal and means for collecting and transmitting said Raman optical signal to a two dimensional charge-coupled device for analysis.

18. A method for using a Surface-Enhanced Raman (SER)-labeled Gene Probe for hybridization, detection and identification of SER-labeled hybridized target oligonucleotide material comprising the steps of:
 a) providing a support means;
 b) exposing said support means to a target sample suspected of containing target oligonucleotide strands of unknown sequence;
 c) incubating said support means with said target sample for a period of time sufficient enough to immobilize said oligonucleotide strands on said support means;
 d) synthesizing SER-labeled gene probes wherein a SER-labeled gene probe comprises at least one oligonucleotide strand of known sequence labeled with at least one SER label unique for said target oligonucleotide strands of a particular sequence, said known oligonucleotide sequence being complementary to said target oligonucleotide strands;
 e) preparing a SER-labeled gene probe solution comprising at least one SER-labeled gene probe;
 f) incubating said support means having said immobilized oligonucleotide strands thereon in an amount of said SER-labeled gene probe solution sufficient enough to provide an amount of SER-labeled gene probes to contact said immobilized oligonucleotide strands, incubating for a time period sufficient as for said SER-labeled gene probes to contact said immobilized oligonucleotide strands and sufficient enough as for hybridization to occur between said SER-labeled gene probe and said immobilized target oligonucleotide, thereby producing SER-labeled hybridized target oligonucleotide material;
 g) removing said oligonucleotide strands that did not hybridize to said immobilized oligonucleotide strands;
 h) activating said support means with a SERS activating means, said support means having SER-labeled hybridized target oligonucleotide material; and
 i) analyzing said SER-activated support means having SER-labeled hybridized target oligonucleotide material.

19. The method of claim 18 wherein said oligonucleotide strands comprise strands of Deoxyribonucleic acid, Ribonucleic acid or peptide nucleic acid.

20. The method of claim 18 wherein said support means is a substrate suitable for hybridization.

21. The method of claim 18 wherein said support means is a membrane suitable for hybridization.

22. The method of claim 18 wherein said support means is a blotting material.

23. The method of claim 18 wherein said support means is a polymer-based nanosphere.

24. The method of claim 18 wherein said support means is an alumina-based nanoparticle.

25. The method of claim 18 wherein said support means is a titanium oxide nanoparticle.

26. The method of claim 18 wherein said support means has a surface comprising cellulose, silica gel or polystyrene.

27. The method of claim 18 wherein said SER activating means comprises the step of coating said support means with a colloidal solution of metal hydrosols to produce metal nanoparticles.

28. The method of claim 27 wherein said metal is silver or gold.

29. The method of claim 18 wherein said SER activating means comprises the step of coating said support means with metal-coated magnetic nanobeads.

30. The method of claim 18 wherein said SER activating means comprises inducing an electrochemical reaction to roughen the surface of said support means on which said hybridization occurs.

31. The method of claim 18 wherein said SER activating means comprises blotting said SERS-labeled hybridized target oligonucleotide material directly onto a SER active support means using a blotting technique.

32. The method of claim 31 wherein said blotting technique comprises applying an electric field to adsorb said SER-labeled hybridized target oligonucleotide material onto a SERS active blot.

33. A method for using a Surface-Enhanced Raman (SER)-labeled Gene Probe for hybridization, detection and identification of SER-labeled hybridized target oligonucleotide material comprising the steps of:
   a) providing a support means;
   b) preparing a solution of gene probe oligonucleotide strands of known sequence, said oligonucleotide strands being complementary to a target oligonucleotide strand;
   c) disposing said gene probe oligonucleotide strands onto said support means;
   d) incubating said support means having said disposed gene probe oligonucleotide strands for a period of time sufficient enough to immobilize said oligonucleotide strands on said support means;
   e) preparing a solution comprising oligonucleotide strands of unknown sequence taken from a target sample containing suspect target oligonucleotide strands, said solution further comprising at least one SER label for a period of time sufficient enough for said target oligonucleotide strands to contact said immobilized gene probe oligonucleotide strands and sufficient enough for hybridization to occur between said immobilized gene probe oligonucleotide strands and said target oligonucleotide strands that are complementary to said immobilized gene probe oligonucleotide strands and sufficient enough as during hybridization, said SER label is intercalated between said hybridized oligonucleotide strands, thereby producing SER-labeled hybridized target oligonucleotide material;
   f) removing said oligonucleotide strands that did not hybridize to said immobilized gene probe oligonucleotide strands;
   g) activating said support means with a SERS activating means, said support means having SER-labeled hybridized target oligonucleotide material; and
   h) analyzing said SERS activated support means having SER-labeled hybridized target oligonucleotide material.

34. The method of claim 33 wherein said oligonucleotide strands comprise strands of Deoxyribonucleic acid, Ribonucleic acid or peptide nucleic acid.

35. The method of claim 33 wherein said support means is a substrate suitable for hybridization.

36. The method of claim 33 wherein said support means is a membrane suitable for hybridization.

37. The method of claim 33 wherein said support means is a blotting material.

38. The method of claim 33 wherein said support means is a polymer-based nanosphere.

39. The method of claim 33 wherein said support means is an alumina-based nanoparticle.

40. The method of claim 33 wherein said support means is a titanium oxide nanoparticle.

41. The method of claim 33 wherein said support means has a surface comprising cellulose, silica gel or polystyrene.

42. The method of claim 33 wherein said SER activating means comprises the step of coating said support means with metal-coated magnetic nanobeads.

43. The method of claim 33 wherein said SER activating means comprises inducing an electrochemical reaction to roughen the surface of said support means on which said hybridization occurs.

44. The method of claim 33 wherein said SER activating means comprises blotting said SERS-labeled hybridized target oligonucleotide material directly onto a SER active support means using a blotting technique.

45. The method of claim 44 wherein said blotting technique comprises applying an electric field to adsorb said SER-labeled hybridized target oligonucleotide material onto a SERS active blot.

46. A method for using a Surface Enhanced Raman (SER)-labeled gene probe for hybridization, detection and identification of SER-labeled hybridized target oligonucleotide material comprising the steps of:
   a) providing a support means;
   b) exposing said support means to a target sample suspected of containing target oligonucleotide strands of unknown sequence;
   c) incubating said support means with said target sample for a period of time sufficient enough to immobilize said oligonucleotide strands on said support means;
   d) preparing a gene probe solution comprising at least one gene probe oligonucleotide strand of known sequence complementary to said target oligonucleotide strands, said solution further comprising at least one SER label in a free state in said solution, said SER label unique for said target oligonucleotide strands of a particular sequence;
   e) incubating said support means having said immobilized oligonucleotide strands thereon in an amount of said gene probe solution sufficient enough to provide enough gene probe oligonucleotide strands to contact said immobilized oligonucleotide strands, incubating for a period of time sufficient as for said gene probe oligonucleotide strands to contact said immobilized oligonucleotide strands and sufficient enough as for hybridization to occur between said gene probe oligonucleotide strands and said complementary immobilized target oligonucleotide strands, and sufficient enough as during hybridization, said SER label is intercalated between said hybridized oligonucleotide strands, thereby producing SER-labeled hybridized target oligonucleotide material;
   f) removing said oligonucleotide strands that did not hybridize to said immobilized oligonucleotide strands;
   g) activating said support means with a SERS activating means, said support means having SER-labeled hybridized target oligonucleotide material; and
   h) analyzing said SER-activated support means having SER-labeled hybridized target oligonucleotide material.

47. The method of claim 46 wherein said oligonucleotide strands comprise strands of Deoxyribonucleic acid, Ribonucleic acid or peptide nucleic acid.

48. The method of claim 46 wherein said support means is a substrate suitable for hybridization.

49. The method of claim 46 wherein said support means is a membrane suitable for hybridization.

50. The method of claim 46 wherein said support means is a blotting material.

51. The method of claim 46 wherein said support means is a polymer-based nanosphere.

52. The method of claim 46 wherein said support means is an alumina-based nanoparticle.

53. The method of claim 46 wherein said support means is a titanium oxide nanoparticle.

54. The method of claim 46 wherein said support means has a surface comprising cellulose, silica gel or polystyrene.

55. The method of claim 46 wherein said SER activating means comprises the step of coating said support means with metal-coated magnetic nanobeads.

56. The method of claim 46 wherein said SER activating means comprises inducing an electrochemical reaction to roughen the surface of said support means on which said hybridization occurs.

57. The method of claim 46 wherein said SER activating means comprises blotting said SERS-labeled hybridized target oligonucleotide material directly onto a SER active support means using a blotting technique.

58. The method of claim 57 wherein said blotting technique comprises applying an electric field to adsorb said SER-labeled hybridized target oligonucleotide material onto a SERS active blot.

59. A method for using a Surface Enhanced Raman (SER)-labeled Gene Probe for hybridization, detection and identification of SER-labeled hybridized target oligonucleotide strands comprising the steps of:
 a) providing a support means;
 b) synthesizing at least one SER-labeled oligonucleotide strand of unknown sequence taken from a target sample being suspect of containing target oligonucleotide strands, said SER-labeled oligonucleotide strand having at least one SER label;
 c) preparing a solution comprising gene probe oligonucleotide strands of known sequence, said oligonucleotide strands being complementary to a target oligonucleotide strand, said solution further comprising at least one SER-labeled oligonucleotide strand wherein said SER label is unique for said target oligonucleotide strand of a particular sequence, and further comprising a SERS activating means;
 d) incubating said support means with said solution for a period of time sufficient enough to immobilize said oligonucleotide strands on said support means while simultaneously allowing hybridization between said gene probe oligonucleotide strands of known sequence and said SER-labeled target oligonucleotide strands to occur, thereby producing SER-labeled hybridized target oligonucleotide material, and simultaneously SERS activating said support means with said SERS activating means; and
 e) analyzing said SERS active support means having SER-labeled hybridized target oligonucleotide material.

60. The method of claim 59 wherein said oligonucleotide strands comprise strands of Deoxyribonucleic acid, Ribonucleic acid or peptide nucleic acid.

61. The method of claim 59 wherein said support means is a substrate suitable for hybridization.

62. The method of claim 59 wherein said support means is a membrane suitable for hybridization.

63. The method of claim 59 wherein said support means is a blotting material.

64. The method of claim 59 wherein said support means is a polymer-based nanosphere.

65. The method of claim 59 wherein said support means is an alumina-based nanoparticle.

66. The method of claim 59 wherein said support means is a titanium oxide nanoparticle.

67. The method of claim 59 wherein said support means has a surface comprising cellulose, silica gel or polystyrene.

68. The method of claim 59 wherein said SERS activating means comprises metal nanoparticles.

69. The method of claim 68 wherein said metal is silver or gold.

70. The method of claim 59 wherein said SERS activating means comprises metal-coated magnetic nanobeads.

71. A method for using a Surface Enhanced Raman (SER)-labeled Gene Probe for hybridization, detection and identification of SER-labeled hybridized target oligonucleotide strands comprising the steps of:
 a) providing a support means;
 b) preparing a solution comprising SER-labeled hybridized target oligonucleotide material comprising at least one SER-labeled oligonucleotide strand of unknown sequence taken from a target sample being suspect of containing target oligonucleotide strands, said SERS label being unique for said target oligonucleotide strand of a particular sequence, and at least one gene probe oligonucleotide strand of known sequence complementary to said target oligonucleotide strand, said gene probe oligonucleotide strand is hybridized with said SER-labeled oligonucleotide strand, said solution further comprising a SERS activating means;
 c) incubating said support means with said solution for a period of time sufficient enough to immobilize said SER-labeled hybridized target oligonucleotide material on said support means while simultaneously SERS activating said support means with said SERS activating means; and
 d) analyzing said SERS active support means having SER-labeled hybridized target oligonucleotide material.

72. The method of claim 71 wherein said oligonucleotide strands comprise strands of Deoxyribonucleic acid, Ribonucleic acid or peptide nucleic acid.

73. The method of claim 71 wherein said support means is a substrate suitable for hybridization.

74. The method of claim 71 wherein said support means is a membrane suitable for hybridization.

75. The method of claim 71 wherein said support means is a blotting material.

76. The method of claim 71 wherein said support means is a polymer-based nanosphere.

77. The method of claim 71 wherein said support means is an alumina-based nanoparticle.

78. The method of claim 71 wherein said support means is a titanium oxide nanoparticle.

79. The method of claim 71 wherein said support means has a surface comprising cellulose, silica gel or polystyrene.

80. The method of claim 71 wherein said SERS activating means comprises metal nanoparticles.

81. The method of claim 80 wherein said metal is silver or gold.

82. The method of claim 71 wherein said SERS activating means comprises metal-coated magnetic nanobeads.

83. The method of claim 71 wherein said SERS activating means comprises delivering reagents onto said support means to form nanoparticles of metal sol directly on said support means.

84. A method for using a Surface-Enhanced Raman (SER)-labeled Gene Probe for hybridization, detection and identification of hybridized target oligonucleotide strands comprising the steps of:
 a) providing a support means;
 b) synthesizing SER-labeled gene probe oligonucleotide strands wherein a SER-labeled gene probe comprises at least one gene probe oligonucleotide strand of known sequence with at least one SER label unique for a target oligonucleotide strand of a particular sequence, said known gene probe oligonucleotide sequence being complementary to said target oligonucleotide strand;
 c) preparing a solution comprising oligonucleotide strands of unknown sequence taken from a target sample being suspect of containing target oligonucleotide strands, said solution further comprising at least one SER-labeled gene probe oligonucleotide strand and a SERS activating means;

d) incubating said support means with said solution for a period of time sufficient enough to immobilize said oligonucleotide strands on said support means while simultaneously allowing hybridization between said target oligonucleotide strands and said SER-labeled gene probe oligonucleotide strand to occur, thereby producing SER-labeled hybridized target oligonucleotide material, and simultaneously SERS activating said support means with said SERS activating means; and e) analyzing said SERS-active support means having SER-labeled hybridized target oligonucleotide material.

85. The method of claim 84 wherein said oligonucleotide strands comprise strands of Deoxyribonucleic acid, Ribonucleic acid or peptide nucleic acid.

86. The method of claim 84 wherein said support means is a substrate suitable for hybridization.

87. The method of claim 84 wherein said support means is a membrane suitable for hybridization.

88. The method of claim 84 wherein said support means is a blotting material.

89. The method of claim 84 wherein said support means is a polymer-based nanosphere.

90. The method of claim 84 wherein said support means is an alumina-based nanoparticle.

91. The method of claim 84 wherein said support means is a titanium oxide nanoparticle.

92. The method of claim 84 wherein said support means has a surface comprising cellulose, silica gel or polystyrene.

93. The method of claim 84 wherein said SERS activating means comprises metal nanoparticles.

94. The method of claim 93 wherein said metal is silver or gold.

95. The method of claim 84 wherein said SERS activating means comprises metal-coated magnetic nanobeads.

96. A method for using a Surface Enhanced Raman (SER)-labeled Gene Probe for hybridization, detection and identification of SER-labeled hybridized target oligonucleotide strands comprising the steps of:

a) providing a support means;

b) synthesizing SER-labeled gene probe oligonucleotide strands comprising at least one gene probe oligonucleotide strand of known sequence with at least one SER label unique for a target oligonucleotide strand of a particular sequence, said known oligonucleotide sequence being complementary to said target oligonucleotide strand;

c) preparing a solution comprising SER-labeled hybridized oligonucleotide target material comprising oligonucleotide strands of unknown sequence taken from a target sample being suspect of containing target oligonucleotide strands, said oligonucleotide strands of unknown sequence hybridized with a SER-labeled gene probe oligonucleotide strand, said solution further comprising a SERS activating means;

d) incubating said support means with said solution for a period of time sufficient enough to immobilize said SER-labeled hybridized target oligonucleotide material on said support means while simultaneously SERS activating said support means with said SERS activating means; and e) analyzing said SERS active support means having SER-labeled hybridized target oligonucleotide material.

97. The method of claim 96 wherein said oligonucleotide strands comprise strands of Deoxyribonucleic acid, Ribonucleic acid or peptide nucleic acid.

98. The method of claim 96 wherein said support means is a substrate suitable for hybridization.

99. The method of claim 96 wherein said support means is a membrane suitable for hybridization.

100. The method of claim 96 wherein said support means is a blotting material.

101. The method of claim 96 wherein said support means is a polymer-based nanosphere.

102. The method of claim 96 wherein said support means is an alumina-based nanoparticle.

103. The method of claim 96 wherein said support means is a titanium oxide nanoparticle.

104. The method of claim 96 wherein said support means has a surface comprising cellulose, silica gel or polystyrene.

105. The method of claim 96 wherein said SERS activating means comprises metal nanoparticles.

106. The method of claim 96 wherein said metal is silver or gold.

107. The method of claim 96 wherein said SERS activating means comprises metal-coated magnetic nanobeads.

* * * * *